United States Patent
Rohland et al.

(10) Patent No.: US 11,458,078 B2
(45) Date of Patent: *Oct. 4, 2022

(54) COLD MANUFACTURED OXIDATIVE HAIR LIGHTENING OR HAIR COLORING COMPOSITION FOR LEVEL 2 COLORS

(71) Applicant: Henkel AG & Co. KGaA, Duesseldorf (DE)

(72) Inventors: Christa Rohland, Duesseldorf (DE); Juergen Schoepgens, Schwalmtal (DE); Gabriele Weser, Neuss (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/254,826

(22) PCT Filed: Jun. 14, 2019

(86) PCT No.: PCT/EP2019/065705
§ 371 (c)(1),
(2) Date: Dec. 21, 2020

(87) PCT Pub. No.: WO2019/243194
PCT Pub. Date: Dec. 26, 2019

(65) Prior Publication Data
US 2021/0259934 A1    Aug. 26, 2021

(30) Foreign Application Priority Data

Jun. 19, 2018   (DE) ................... 10 2018 209 891.3

(51) Int. Cl.
| | | |
|---|---|---|
| A61Q 5/10 | (2006.01) | |
| A61K 8/22 | (2006.01) | |
| A45D 19/00 | (2006.01) | |
| A61K 8/06 | (2006.01) | |
| A61K 8/23 | (2006.01) | |
| A61K 8/24 | (2006.01) | |
| A61K 8/31 | (2006.01) | |
| A61K 8/34 | (2006.01) | |
| A61K 8/368 | (2006.01) | |
| A61K 8/41 | (2006.01) | |
| A61K 8/46 | (2006.01) | |
| A61K 8/67 | (2006.01) | |
| A61K 8/81 | (2006.01) | |
| A61Q 5/08 | (2006.01) | |

(52) U.S. Cl.
CPC ............ *A61K 8/22* (2013.01); *A45D 19/0066* (2021.01); *A61K 8/064* (2013.01); *A61K 8/23* (2013.01); *A61K 8/24* (2013.01); *A61K 8/31* (2013.01); *A61K 8/342* (2013.01); *A61K 8/368* (2013.01); *A61K 8/416* (2013.01); *A61K 8/463* (2013.01); *A61K 8/676* (2013.01); *A61K 8/8152* (2013.01); *A61Q 5/08* (2013.01); *A61Q 5/10* (2013.01)

(58) Field of Classification Search
CPC ... A61Q 5/10; A61Q 5/08; A61K 8/22; A61K 2800/882; A61K 2800/88; A61K 8/34; A61K 8/37; A61K 2800/48; A61K 8/92; A61K 2800/594; A61K 8/062; A61K 8/342; A61K 8/416; A61K 8/463; A61K 8/8152
USPC ............................................................ 8/405
See application file for complete search history.

(56) References Cited

U.S. PATENT DOCUMENTS

| | | | | |
|---|---|---|---|---|
| 2009/0070945 | A1* | 3/2009 | Nguyen ................... | A61K 8/31 8/431 |
| 2013/0156716 | A1* | 6/2013 | Yontz ..................... | A61Q 5/065 424/70.6 |
| 2016/0158125 | A1* | 6/2016 | Neuba ...................... | A61K 8/22 424/62 |
| 2017/0273879 | A1 | 9/2017 | Witte et al. | |
| 2018/0168942 | A1* | 6/2018 | Schoepgens ............. | A61K 8/86 |
| 2019/0175459 | A1 | 6/2019 | Mueller et al. | |
| 2020/0323763 | A1 | 10/2020 | Schoepgens et al. | |

FOREIGN PATENT DOCUMENTS

| | | |
|---|---|---|
| DE | 102014226540 A1 | 6/2016 |
| EP | 3108872 A1 | 12/2016 |
| WO | 2018028861 A1 | 2/2018 |
| WO | 2019115058 A1 | 6/2019 |

OTHER PUBLICATIONS

EPO, International Search Report issued in International Application No. PCT/EP2019/065705, dated Sep. 20, 2019.

* cited by examiner

*Primary Examiner* — Eisa B Elhilo
(74) *Attorney, Agent, or Firm* — Lorenz & Kopf, LLP

(57) ABSTRACT

The subject matter of the present disclosure are agents for oxidative hair lightening or hair coloring, containing from about 70-90% by weight of a total of % of water, alkalizing agent, optionally a colorant, and a certain mixture of a cross-linked copolymer of acrylic acid and non-ethoxylated esters of acrylic acid with linear C10-C30 monoalcohols, anionic surfactant and linear, saturated C8-C22 alkan-1-ol, and sodium polyacrylate, whereby the brightening or coloring agent obtains an application-technically optimal viscosity and the consistency of a gel-like cream with an excellent haptics.

20 Claims, No Drawings

1

COLD MANUFACTURED OXIDATIVE HAIR LIGHTENING OR HAIR COLORING COMPOSITION FOR LEVEL 2 COLORS

CROSS-REFERENCE TO RELATED APPLICATION

This application is a U.S. National-Stage entry under 35 U.S.C. § 371 based on International Application No. PCT/EP2019/065705, filed Jun. 14, 2019, which was published under PCT Article 21(2) and which claims priority to German Application No. 10 2018 209 891.3, filed Jun. 19, 2018, which are all hereby incorporated in their entirety by reference.

TECHNICAL FIELD

The present application concerns an oxidative hair-lightening- or hair dyeing in cream form, a kit comprising this hair-lightening- or hair dyeing and a hair-lightening-or-hair dyeing process using this hair-lightening- or hair dyeing.

BACKGROUND

So-called oxidation brightening agents are used to lighten or bleach hair. So-called oxidation dyes are used for permanent, intensive dyeing's with corresponding fastness properties. Such dyes usually contain oxidation dye precursors, so-called developer components and coupler components. Under the influence of oxidizing agents or atmospheric oxygen, the developer components form the actual dyes among themselves or when coupled with one or more coupler components. The oxidation dyes are exemplified by excellent, long-lasting dyeing results. For natural looking dyeing's, usually a mixture of a larger number of oxidation dye precursors (OFV) must be used. Frequently, hair lightening or hair dye products also contain at least one direct dyestuff (DZ) to nuance or matt unwanted shades of the melanin decomposition products.

In most cases, oxidative hair whitening and hair dyeing products have an alkaline pH value for stabilizing the dye precursors during storage and for accelerating the reaction during oxidative application, which is adjusted with alkalizing agents such as alkanolamines, ammonia or inorganic bases.

To form the dye, the alkaline dye component is usually mixed with an aqueous hydrogen peroxide solution to form a homogeneous cream or gel and then applied directly to the hair to be dyed. To lighten the hair by the oxidative breakdown of the natural hair dye melanin, the alkaline lightening component is usually mixed with an aqueous hydrogen peroxide solution to form a homogeneous cream or gel and applied directly afterwards to the hair to be bleached. The coloring or lightening mixture remains on the hair for a period of from about 5 to about 60 minutes until the oxidative formation of the dye on the hair or the breakdown of melanin is completed. The dyeing or brightening mixture is then washed out.

The pH value of the lightening or coloring agent can be used to control the degree of color change or lightening of the hair. In addition, the pH value of the lightening or coloring agent can also be used to consider the quality of the hair to be lightened or dyed. For thin or pre-damaged hair, in contrast to strong or undamaged hair, a rather weakly acidic to weakly alkaline environment is sufficient for lightening or coloring. In a more alkaline medium, lightening or coloring of thin or previously damaged hair can be more intense than desired. The hair is also further damaged by strong alkaline agents. A lightening or coloring carried out in a weakly acidic or weakly alkaline environment also offers the possibility of a so-called Level 2 coloring, i.e. a coloring in pastel shades which is more easily washed out or over-colored than a stronger Level 3 coloring, thus allowing the consumer to change hair color more quickly.

The above-mentioned oxidation dye precursors (OFV) and alkalizing agents are usually incorporated in a cosmetically suitable carrier, such as a cream. The carrier ensures a homogeneous distribution and sufficient dwell time of the hair brightener or hair dye on the hair. Many OFV are aromatic amine compounds. Some of the commonly used OFV, such as p-toluenediamine or ,5-diamino-1-(2-hydroxyethyl)pyrazole, are only stable or can be used on a large scale in the form of their salts, especially as sulphate. Their addition thus increases the electrolyte concentration in the carrier. This can lead to a destabilization of the gel or cream carrier. The carrier of the agent as contemplated herein must therefore have a good tolerance to higher electrolyte concentrations. Furthermore, the carrier must have a viscosity suitable for the application even after dilution with the aqueous oxidant composition. Cream carriers with a too high content of high-melting fat components, such as fatty alcohols, often show a particularly sharp drop in the viscosity of the application mixture compared to the oxidant-free carrier.

BRIEF SUMMARY

Agents for oxidative hair lightening or hair coloring as well as kits-of-parts processing units and processes for oxidative hair lightening or hair coloring are provided herein. In an embodiment, an agent for oxidative hair lightening or hair coloring comprises, in each case based on the weight of the agent, from about 70-90% by weight water,
at least one alkalizing agent,
at least one crosslinked copolymer of acrylic acid and non-ethoxylated esters of acrylic acid with linear C10-C30 monoalcohols as monomers, the crosslinked copolymer being present in a total amount of from about 0.2-0.6% by weight,
at least one linear, saturated 1-alkanol with one hydroxy group and from about 8 to about 22 carbon atoms in a total amount of from about 0.3-1.5% by weight,
at least one anionic surfactant in a total amount of from about 1-6% by weight, and
optionally at least one coloring substance selected from oxidation dye precursors, direct-acting hair dyes and mixtures thereof,
sodium polyacrylate,
wherein the agent is free from oxidizing agents, and
wherein the agent has a pH value in the range from about 7.5 to about 9.5, measured at 20° C.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure was based on the task of providing an oxidative hair lightening or hair dyeing agent which can be produced under the most economical and sustainable conditions. Furthermore, the present disclosure was based on the task of providing an oxidative hair lightening- or hair dye which is easy to mix and apply.

Furthermore, the present disclosure was based on the task of providing an oxidative hair whitening or hair dye which has a cream-like consistency, feel and appearance without a higher content of high melting fat components.

Furthermore, the present disclosure was based on the task of providing an oxidative hair dye with good tolerance to higher electrolyte concentrations.

Furthermore, the present disclosure was based on the task of providing an oxidative hair dye for a level 2 coloration.

These tasks are solved by an agent for oxidative hair lightening or hair coloring, which contains the following, in each case based on its weight:
- from about 70-90% by weight, preferably from about 73-86% by weight, particularly preferably from about 76-84% by weight, water,
- at least one alkalizing agent,
- at least one crosslinked copolymer composed of acrylic acid and non-ethoxylated esters of acrylic acid with linear C10-C30 monoalcohols as monomers, the crosslinked copolymer being present in a total amount of from about 0.2-0.6% by weight, preferably from about 0.3-0.5% by weight, particularly preferably from about 0.4-0.45% by weight, in each case based on the weight of the agent,
- at least one linear, saturated 1-alkanol with one hydroxy group and 8 to 22 carbon atoms in a total amount of from about 0.3-1.5% by weight, preferably from about 0.4-1.2% by weight, particularly preferably from about 0.5-1.0% by weight, extremely preferably from about 0.6-0.8% by weight, and
- at least one anionic surfactant in a total amount of from about 1-6% by weight, preferably from about 2-5% by weight, and particularly preferably from about 2.5-4.5% by weight,
- optionally at least one coloring substance selected from oxidation dye precursors, direct-acting hair dyes and mixtures thereof, whereby no oxidizing agents are contained,
Sodium polyacrylate, preferably with a mass-average molar mass Mw in the range of from about 1,000,000 to about 20,000,000 Daltons, particularly preferably from about 6,000,000 to about 15,000,000 Daltons, preferably in a total amount of from about 0.1-1.5 wt.-%, preferably from about 0.5-1.3% by weight, particularly preferably from about 0.8-1.1% by weight, in each case based on the weight of the agent, wherein particularly preferably the sodium polyacrylate is contained as pregelled in a water-in-oil emulsion, and wherein the agent has a pH value in the range from about 7.5 to about 9.5, preferably in the range from about 8.0 to about 9.0, each measured at 20° C.

The product as contemplated herein represents the alkaline dyeing component of an oxidative hair lightening or hair dyeing product. This is usually mixed with an aqueous hydrogen peroxide preparation immediately before use and then applied to the hair to be lightened or dyed. Until mixed with the aqueous hydrogen peroxide preparation, the agent of the present disclosure contains no oxidizing agents.

Water Content

The agent as contemplated herein contains, in each case based on its weight, from about 70-90% by weight, preferably from about 73-86% by weight, particularly preferably from about 76-84% by weight, of water.

Alkalizing Agent

The agent as contemplated herein contains at least one alkalizing agent. The alkalizing agent preferred to adjust the preferred pH is selected from the group comprising ammonium hydroxide, basic amino acids, alkali hydroxides, alkanolamines, alkali metal metasilicates, alkali phosphates and alkali hydrogen phosphates and mixtures thereof. The preferred alkali metal ions are lithium, sodium, potassium, especially sodium or potassium.

The basic amino acids usable as alkalizing agents are preferably selected from the group L-arginine, D-arginine, D,L-arginine, L-lysine, D-lysine, D,L-lysine, particularly preferably L-arginine, D-arginine, D,L-arginine as an alkalizing agent as contemplated herein.

The alkali hydroxides that can be used as alkalizing agents are preferably selected from sodium hydroxide and potassium hydroxide.

The alkanolamines which can be used as alkalizing agents are preferably selected from primary amines with a $C_2$-$C_6$ alkyl base body which carries at least one hydroxyl group. Particularly preferred alkanolamines are selected from the group formed by 2-aminoethan-1-(monoethanolamine), 3-aminopropan-1-ol, 4-aminobutan-1-ol, 5-aminopentan-1-ol, 1-aminopropan-2-ol, 1-Aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1.2-diol, 2-amino-2-methylpropan-1.3-diol. Alkanolamines particularly preferred as contemplated herein are selected from the group 2-aminoethan-1-ol, 2-amino-2-methylpropan-1-ol and 2-amino-2-methyl-propan-1.3-diol.

A particularly preferred alkalizing agent as contemplated herein is monoethanolamine (2-aminoethan-1-ol). To achieve a dyeing process which is as odorless as possible and to optimize the fastness properties of the dyeing, monoethanolamine is contained in a total amount of from about 0.2-4% by weight, preferably from about 0.5-3% by weight, more preferably from about 1 to about 2.5% by weight and particularly preferably from about 1.5 to about 2% by weight—based on the weight of the brightening or coloring agent as contemplated herein.

In addition to or instead of monoethanolamine, other preferred brightening and coloring agents as contemplated herein contain ammonium hydroxide, i.e. ammonia in the form of its aqueous solution. The corresponding aqueous ammonia solutions can be from about 10 to about 35 percent solutions (calculated in volume %. 100 g aqueous ammonia solution with about 25% by volume $NH_3$ contains about 50 g ammonia. Preferably, ammonia is used in the form of a from about 20 to about 30 volume percent solution, especially preferred in the form of about 25-volume percent solution.

In a particularly preferred form, the whitening or coloring agent as contemplated herein contains ammonium hydroxide in an amount of from about 0.2 to about 6% by weight, preferably from about 0.3 to about 5% by weight, more preferably from about 0.5 to about 3% by weight and particularly preferably from about 1 to about 2% by weight, based on the weight of the whitening or coloring agent as contemplated herein.

Furthermore, other alkalizing agents such as potassium hydroxide and sodium hydroxide may be contained, preferably in a total amount of from about 0.05 to about 1.5% by weight, particularly preferably from about 0.1 to about 0.6% by weight, in each case based on the weight of the brightening or coloring agent as contemplated herein.

In another particularly preferred form, the brightening or coloring agent of the present disclosure contains at least one alkalizing agent selected from the group comprising alkanolamines, potassium hydroxide, sodium hydroxide and mixtures thereof.

In another particularly preferred form, the brightening or coloring agent as contemplated herein contains at least one alkalizing agent in a total amount of from about 0.02-0.4 mol/100 g, preferably from about 0.05-0.3 mol/100 g, in each case in mol of alkalizing agent per about 100 grams of the agent as contemplated herein.

The agents as contemplated herein are exemplified by a pH value in the range from about 7.5 to about 9.5, preferably in the range from about 8.0 to about 9.0, each measured at 20° C.

A further notable feature of the compositions as contemplated herein is the content of at least one crosslinked copolymer built up from acrylic acid and non-ethoxylated esters of acrylic acid with linear C10-C30 monoalcohols as monomers, the crosslinked copolymer being contained in a total amount of from about 0.2-0.6% by weight, preferably from about 0.3-0.5% by weight, particularly preferably from about 0.4-0.45% by weight, in each case based on the weight of the composition. At least one crosslinked copolymer of acrylic acid and non-ethoxylated esters of acrylic acid with linear C10-C30 monoalcohols is preferably selected from copolymers with the INCI name Acrylates/C10-30 Alkyl Acrylate Crosspolymer. Sucrose allyl ether or pentaerythrityl allyl ether is preferably contained as the crosslinking agent.

Cross-linked copolymers of acrylic acid and non-ethoxylated esters of acrylic acid with linear C10-C30 monoalcohols, which are particularly preferred as contemplated herein, are obtainable by polymerization of a monomer mixture which contains—in each case based on its weight—from about 80 to about 99 wt. % of a monomer mixture which is %, preferably from about 90 to about 98% by weight, of acrylic acid, at least one non-ethoxylated ester of acrylic acid with linear C10-C30 monoalcohols in a total amount of from about 0.9-19.9% by weight, preferably from about 2-10% by weight, and at least one crosslinking agent in a total amount of from about 0.1-4% by weight.

Other crosslinked copolymers of acrylic acid and non-ethoxylated esters of acrylic acid with linear C10-C30 monoalcohols which are particularly preferred as contemplated herein are exemplified in that their 0.5% by weight dispersion in water at 25° C. and a pH in the range from about 5.8-6.3 has a viscosity in the range from about 45,000 to 65,000 mPas, measured with a Brookfield RVF or Brookfield RVT viscometer at a rotation frequency of 20 min$^{-1}$ with spindle #7.

The content of the at least one crosslinked copolymer composed of acrylic acid and non-ethoxylated esters of acrylic acid with linear C10-C30 monoalcohols as monomers is selected such that the viscosity of the agent as contemplated herein is preferably in the range of from about 3,000-25,000 mPas, preferably from about 4,000-20,000 mPas, particularly preferably from about 6,000 to about 12,000 mPas, in each case measured at 20° C. with a Haake VT 550 viscometer with the measuring system SV.

The agents as contemplated herein and used as contemplated herein further contain at least one linear, saturated 1-alkanol with one hydroxy group and 8 to 22 carbon atoms in a total amount of from about 0.3-1.5 wt. %, preferably from about 0.4-1.2 wt. %, particularly preferably from about 0.5-1.0 wt. %, extremely preferably from about 0.6-0.8 wt. %, each based on the weight of the agent. As contemplated herein, this is at least one linear, saturated 1-alkanol with a hydroxy group and 8 to 22 carbon atoms selected from 1-decanol, 1-dodecanol (lauryl alcohol), 1-tridecanol, 1-tetradecanol (myristyl alcohol), 1-hexadecanol (cetyl alcohol), 1-octadecanol (stearyl alcohol), 1-eicosanol (arachyl alcohol) and 1-docosanol (behenyl alcohol) and mixtures thereof. As contemplated herein, a preferred alkanol mixture is coconut alcohol, i.e. alkanol mixtures obtained by hydrogenation of coconut oil. A coconut alcohol, which as contemplated herein is particularly preferred, has the following chain length distribution in relation to its weight: $C_{10}$ and shorter: zero to a maximum of about 3% by weight, $C_{12}$: 48-58% by weight, $C_{14}$: 18-24 weight %, $C_{16}$: 8-12 weight %, $C_{18}$: 11-15% by weight, $C_{20}$: zero to maximum 1% by weight. $C_5$-$C_{22}$ alkane-1-ols are selected from lauryl alcohol, coconut alcohol, 1-tetradecanol (myristyl alcohol), cetyl alcohol and stearyl alcohol as well as mixtures thereof, especially from coconut alcohol and lauryl alcohol.

For the purposes of the present application, the above-mentioned linear, saturated 1-alkanols with one hydroxy group are not considered to be surfactants either with regard to the agents and compositions (M1) or with regard to the oxidizing preparations (M2) of the present disclosure.

Anionic Surfactant

The agents according to and used as contemplated herein contain at least one anionic surfactant in a total amount of from about 1-6 wt. %, preferably from about 2-5 wt. %, and particularly preferably from about 2.5-4.5 wt. %, each based on the weight of the agent.

For the purposes of the present application, surfactants and emulsifiers are amphiphilic (bifunctional) compounds which include at least one hydrophobic and at least one hydrophilic part of the molecule.

For the purposes of the present application, saturated and unsaturated alkane-1-ols with at least 4 carbon atoms in the alk(en)yl radical and glyceryl fatty acid mono- and diesters with at least 4 carbon atoms in the fatty acid radical are not counted as surfactants.

The hydrophobic radical is preferably a hydrocarbon chain with 8-30 carbon atoms, which can be saturated or unsaturated, linear, or branched. This $C_8$-$C_{30}$-Alkyl chain is particularly preferably linear. The basic properties of the surfactants and emulsifiers are oriented adsorption at interfaces as well as aggregation to micelles and the formation of lyotropic phases.

When selecting surfactants as contemplated herein, it may be preferable to use a mixture of surfactants to optimally adjust the properties of the oxidative brightening or coloring agents as contemplated herein.

As anionic surfactants, all anionic surface-active substances suitable for use on the human body, which have a water-solubilizing, anionic group, for example a sulphate, sulphonate or phosphate group, and a lipophilic alkyl group with about 8 to 30 C atoms, preferably 8 to 24 C atoms in the molecule, are suitable as contemplated herein. In addition, glycol or polyglycol ether groups, ester, ether and amide and hydroxyl groups may also be present in the molecule. Examples of suitable anionic surfactants are, in each case in the form of the sodium, potassium and ammonium as well as the mono-, di- and trialkanolammonium salts with 2 to 4 C atoms in the alkanol group, polyethoxylated ether carboxylic acids, acyl sarcosides, acyl taurides, acyl isethionates, Sulphosuccinic acid mono- and dialkyl esters and sulphosuccinic acid mono-alkyl polyoxyethyl esters with 1 to 6 ethylene oxide groups, linear alkane sulphonates, linear alpha-olefin sulphonates, sulphonates of unsaturated fatty acids with up to 6 double bonds, alphasulpho fatty acid methyl esters of fatty acids, $C_8$-$C_{20}$ alkyl sulphates and $C_8$-$C_{20}$ alkyl ether sulphates containing 1 to 15 oxyethyl groups, mixtures of surface-active hydroxysulphonates, sulphated hydroxyalkyl polyethylene and/or hydroxyalkylenepropylene glycol ethers, esters of tartaric acid or citric acid with ethoxylated or propoxylated fatty alcohols, optionally polyethoxylated alkyl and/or alkenyl ether phosphates, sulphated fatty acid alkylene glycol esters, linear and branched fatty acids with 8 to 30 C atoms and their salts (soaps), and monoglyceride sulphates and monoglyceride ether sulphates. Preferred anionic surfactants are selected from $C_8$-$C_{20}$-Alkyl sulphates, $C_8$-$C_{20}$-Alkyl ether sulphates and $C_8$-$C_{20}$-Ether carboxylic acids, each with 8 to 20 C atoms in the alkyl group and 0 to 12 ethylene oxide groups in the molecule. Sodium laureth sulphate with 1 to 3, particularly preferably 2, ethylene oxide groups in the molecule is particularly preferred.

Compositions which are extraordinarily preferred as contemplated herein contain at least one anionic surfactant selected from $C_8$-$C_{20}$ alkyl sulphates, $C_8$-$C_{20}$ alkyl ether sulphates and $C_8$-$C_{20}$ ether carboxylic acids, in each case having 8 to 20 C atoms in the alkyl group and 0 to 12 ethylene oxide groups in the molecule, sodium laureth sulphate having 1 to 3, particularly preferably 2, ethylene oxide groups in the molecule, in a total amount of from about 1-6 wt. % of the surfactant. % by weight, preferably from about 2-5% by weight, and particularly preferably from about 2.5-4.5% by weight, in each case based on the weight of the agent, is particularly preferred.

Non-Ionic Surfactant

In a preferred embodiment of the present disclosure, agents which are as contemplated herein and used as contemplated herein contain at least one non-ionic surfactant. Particularly preferably, at least one nonionic surfactant is contained in a total amount of from about 0.01-1 wt. %, preferably from about 0.05-0.5 wt. %, and particularly preferably from about 0.1-0.3 wt. %, each based on the weight of the agent.

The non-ionic surfactants suitable for use on the human body as contemplated herein are all non-ionic surface-active substances suitable for use on the human body, which have at least one water-solubilizing, non-ionic group, in particular a polyethylene glycol ether group with at least 2 ethylene oxide units, a glycoside group, in particular a glucose or methyl glucose group, a polyglycoside group with on average more than one glycoside unit, a polyglycerol group with at least two glycerol units, a sorbitan group, an amide group or several different ones of these groups, for example a sorbitan group and a polyethylene glycol ether group, and a lipophilic alkyl group with about 8 to 30 C atoms, preferably 10 to 24 C atoms. Nonionic surfactants which are used with particular preference are selected from those containing 7-80 moles of ethylene oxide per mole of ethoxylated castor oil, ethoxylated $C_8$-$C_{30}$ alkanols with 4-100 moles of ethylene oxide per mole, ethoxylated $C_8$-$C_{30}$ carboxylic acids with 5-30 moles of ethylene oxide per mole, with 4-50 moles of ethylene oxide per mole of ethoxylated sorbitan monoesters of linear saturated and unsaturated $C_{12}$-$C_{30}$ carboxylic acids, which may be hydroxylated, in particular those of myristic acid, palmitic acid, stearic acid or mixtures of these fatty acids, alkyl mono- and -oligoglycosides containing from 8 to 22 carbon atoms in the alkyl radical and their ethoxylated analogues, and mixtures of the above-mentioned substances.

The ethoxylated $C_8$-$C_{30}$-Alkanols have the formula $R^1O(CH_2CH_2O)_nH$, where $R^1$ stands for a linear or branched alkyl and/or alkenyl radical with 8-30 carbon atoms and n, the average number of ethylene oxide units per molecule, for numbers from 4-100, preferably 6-30, particularly preferably 12 to 20 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, Isostearyl alcohol, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Also adducts of 10-100 moles of ethylene oxide with technical fatty alcohols with 12-18 carbon atoms, such as coconut, palm, palm kernel or tallow fatty alcohol, are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30 are particularly preferred and Coceth-10, Coceth-12, Coceth-15, Coceth-20 and Coceth-30; Ceteth-10, Ceteth-12, Ceteth-15, Ceteth-20, Ceteth-30, Steareth-10, Steareth-12, Steareth-15, Steareth-20 and Steareth-30 and mixtures thereof are particularly preferred.

The ethoxylated $C_8$-$C_{30}$-Carboxylic acids have the formula $R^1O(CH_2CH_2O)_nH$, where $R^1O$ stands for a linear or branched saturated or unsaturated acyl radical with 8-30 carbon atoms and n, the average number of ethylene oxide units per molecule, for numbers of 5-30, preferably 6-20, particularly preferably 6 to 12 moles of ethylene oxide with 1 mole of $C_8$-$C_{30}$-Carboxylic acid, which is preferably selected from caprylic acid, 2-Ethylhexanoic acid, capric acid, lauric acid, isotridecanoic acid, myristic acid, cetylic acid, palmitoleic acid, stearic acid, isostearic acid, Oleic acid, elaidic acid, petroselinic acid, arachyic acid, gadoleic acid, behenic acid, erucic acid and brassidic acid and from their technical mixtures. Adducts of 5-30, preferably 6-20, particularly preferably 6 to 12 mol ethylene oxide of technical fatty acids with 12-18 carbon atoms, such as coconut, palm, palm kernel or tallow fatty acid, are also suitable.

Alkyl mono- and -oligoglycosides with 8 to 22 carbon atoms in the alkyl radical are known non-ionic surfactants corresponding to formula (I),

$$R^1O\text{-}[G]_p \qquad (I)$$

in which $R^1$ is an alkyl or alkenyl radical containing 8 to 22 carbon atoms, G is a sugar residue containing 5 or 6 carbon atoms and p is several 1 to 10. The alkyl and alkenyl oligoglycosides can be derived from aldoses or ketoses with 5 or 6 carbon atoms, preferably glucose. The preferred alkyl and/or alkenyl oligoglycosides are therefore alkyl and/or alkenyl oligoglucosides. The index number p in the general formula (I) indicates the degree of oligomerization (DP), i.e. the distribution of mono- and oligoglycosides, and is a number between 1 and 10. While p in the individual molecule must always be an integer and can assume the values p=1 to 6, the value p for a particular alkyl oligoglucoside is an analytically determined arithmetical quantity, which usually represents a fractional number. Preferably alkyl and/or alkenyl oligoglycosides with an average degree of oligomerization p of from about 1.1 to about 3.0 are used. Preference is given to those alkyl and/or alkenyl oligoglycosides whose degree of oligomerization is less than about 1.7 and lies in the range from about 1.2 to about 1.4. The alkyl or alkenyl radical $R^1$ can be derived from primary alcohols containing 4 to 22, preferably 8 to 22 carbon atoms. Typical examples are caprylic alcohol, caprine alcohol, undecrylic alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, natural fatty alcohols such as coconut alcohol and technical mixtures. Examples of commercially available alkyl oligoglucoside products are the Oramix® grades from Seppic, for example Oramix® NS 10, and the Plantacare® grades from BASF, for example Plantacare® 2000UP, Plantacare® 1200UP, Plantacare® 810UP and Plantacare® 818UP. Also particularly preferred is cocoglucoside, a non-ionic surfactant corresponding to formula (I) above in which $R^1$ represents coco alkyl radicals containing 8 to 16 carbon atoms, G represents a glucose residue and p is a number ranging from about 1.2 to about 1.4.

Compositions which are extraordinarily preferred as contemplated herein contain at least one non-ionic surfactant selected from those containing 7-80 moles of ethylene oxide per mole of ethoxylated castor oil, ethoxylated $C_8$-$C_{30}$ alkanols with 6-30, preferably 12 to 20 moles of ethylene oxide per mole, ethoxylated $C_8$-$C_{30}$ carboxylic acids with 5-30 moles of ethylene oxide per mole with 4-50 mol ethylene oxide per mol ethoxylated sorbitan monoesters of linear saturated and unsaturated $C_{12}$-$C_{30}$-carboxylic acids which may be hydroxylated, alkyl mono- and -oligoglycosides having 8 to 22 carbon atoms in the alkyl radical, and mixtures of the above mentioned substances, in a total amount of from about 0.01-1% by weight.-%, preferably from about 0.05-0.5% by weight, and particularly preferably from about 0.1-0.3% by weight, each based on the weight of the agent.

Further agents which are as contemplated herein extremely preferred contain a mixture of sodium laureth sulfate with 1 to 3, particularly preferably 2, ethylene oxide groups in the molecule and at least one non-ionic surfactant selected from ethoxylated $C_8$-$C_{30}$ alkanols with 6-30, preferably 12 to 20 moles of ethylene oxide per mole, and alkyl mono- and oligoglycosides with 8 to 22 carbon atoms in the alkyl radical in a total amount of from about 1.01-7 wt. %. %, preferably from about 2.05-5.5 wt. %, and particularly preferably from about 2.6-4.8 wt. %, in each case based on the weight of the agent.

Furthermore, the agents as contemplated herein contain sodium polyacrylate. As contemplated herein, sodium polyacrylate is preferably understood to mean polymers with the CAS number 9003-04-7. Sodium polyacrylates preferred as contemplated herein have a weight-average molecular weight $M_w$ in the range from about 1,000,000 to about 20,000,000 daltons, preferably from about 6,000,000 to about 15,000,000 daltons. The average molecular weight $M_w$ can be determined for example by gel permeation chromatography (GPC) with polystyrene as the internal standard in accordance with DIN 55672-3, Version 8/2007.

The mixture of cross-linked copolymer of acrylic acid and non-ethoxylated esters of acrylic acid with linear C10-C30 monoalcohols, linear, saturated C8-C22 alkan-1-ol, anionic surfactant and sodium polyacrylate as contemplated herein leads to a thickening of the agent with application-technically optimal viscosity, while at the same time maintaining the consistency of a gel-like cream with excellent haptics.

Present disclosureally extremely preferred agents contain sodium polyacrylate in a total amount of from about 0.1-1.5% by weight, preferably from about 0.5-1.3% by weight, particularly preferably from about 0.8-1.1% by weight, each based on the weight of the agent.

In a particularly preferred version, the sodium polyacrylate is contained as sodium polyacrylate pre-gelled in a water-in-oil emulsion. Here it is particularly preferred that the sodium polyacrylate-containing water-in-oil emulsion contains, in each case based on its weight, from about 40-60% by weight of sodium polyacrylate, a total of from about 25-45% by weight of oil(s), a total of from about 0.5-4.9% by weight of surfactant(s) and from about 0.5-4.9% by weight of water.

Particularly preferred is the oil contained in the sodium polyacrylate-containing water-in-oil emulsion selected from natural and synthetic hydrocarbons, particularly preferably mineral oil, paraffin oils, $C_{18}$-$C_{30}$ isoparaffins, especially isoeicosane, polyisobutenes and polydecenes, $C_8$-$C_{16}$ isoparaffins, as well as 1,3-di(2-ethylhexyl)-cyclohexane; branched alkanols containing a hydroxy group and 10 to 50 carbon atoms; the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{15}$ alkanols or with polyvalent linear or branched $C_2$-$C_6$ alkanols; silicone oils and mixtures of the above substances. A particularly preferred oil as contemplated herein is mineral oil.

Particularly preferred is at least one surfactant selected from nonionic surfactants contained in the sodium polyacrylate-containing water-in-oil emulsion. Non-ionic surfactants used with particular preference are selected from 7-80 moles of ethylene oxide per mole of ethoxylated castor oil, ethoxylated $C_8$-$C_{24}$-Alkanols with 5-30 moles of ethylene oxide per mole, ethoxylated $C_8$-$C_{24}$-Carboxylic acids with 5-30 moles of ethylene oxide per mole, with 4-50 moles of ethylene oxide per mole of ethoxylated sorbitan monoesters of linear saturated and unsaturated $C_{12}$-$C_{30}$-Carboxylic acids, which can be hydroxylated, especially those of myristic acid, palmitic acid, stearic acid or of mixtures of these fatty acids, alkyl mono- and oligoglycosides with 8 to 22 carbon atoms in the alkyl radical and their ethoxylated analogues, and mixtures of the aforementioned substances.

The ethoxylated $C_8$-$C_{24}$-Alkanols have the formula $R^1O(CH_2CH_2O)_nH$, where $R^1$ stands for a linear or branched alkyl and/or alkenyl radical with 8-24 carbon atoms and n, the average number of ethylene oxide units per molecule, for numbers from 5-30, preferably 6-20, particularly preferably 6 to 12 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, isostearyl alcohol, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Also adducts of 10-100 moles of ethylene oxide with technical fatty alcohols with 12-18 carbon atoms, such as coconut, palm, palm kernel or tallow fatty alcohol, are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth -30, Ceteth-10, Ceteth-12, Ceteth-15, Ceteth-20, Ceteth-30, Steareth-10, Steareth-12, Steareth -15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30 and Coceth-10, Coceth -12, Coceth-15, Coceth-20 and Coceth-30; trideceth-6 and isotrideceth-6 and mixtures thereof are particularly preferred.

The ethoxylated $C_8$-$C_{24}$-Carboxylic acids have the formula $R^1O(CH_2CH_2O)_nH$, where $R^1O$ stands for a linear or branched saturated or unsaturated acyl radical with 8-24 carbon atoms and n, the average number of ethylene oxide units per molecule, for numbers of 5-30, preferably 6-20, particularly preferably 6 to 12 moles of ethylene oxide with 1 mole of $C_8$-$C_{24}$-Carboxylic acid, which is preferably selected from caprylic acid, 2-Ethylhexanoic acid, capric acid, lauric acid, isotridecanoic acid, myristic acid, cetylic acid, palmitoleic acid, stearic acid, isostearic acid, Oleic acid, elaidic acid, petroselinic acid, arachyic acid, gadoleic acid, behenic acid, erucic acid and brassidic acid and from their technical mixtures. Adducts of 5-30, preferably 6-20, particularly preferably 6 to 12 mol ethylene oxide of technical fatty acids with 12-18 carbon atoms, such as coconut, palm, palm kernel or tallow fatty acid, are also suitable.

Agents which are extraordinarily preferred as contemplated herein contain at least one sodium polyacrylate with a mass-average molar mass $M_w$ in the range from about 1,000,000 to about 20,000,000 Dalton, preferably from about 6,000,000 to about 15,000,000 Dalton, in a total amount of from about 0.1-1.5% by weight, preferably from about 0.5-1.3% by weight, particularly preferably from about 0.8-1.1% by weight, each based on the weight of the agent, wherein the sodium polyacrylate is contained as pregelled in a water-in-oil emulsion, said water-in-oil emulsion containing 40-60% by weight, each based on its weight, of sodium polyacrylate, from about 25-45% by weight in total of oil(s), preferably mineral oil, from about 0.5-4.9% by weight in total of surfactant(s), preferably from about 0.5-4.9% by weight of niotenside(s), and from about 0.5-4.9% by weight of water.

The combination of the cross-linked copolymer of acrylic acid and non-ethoxylated esters of acrylic acid with linear C10-C30 monoalcohols, linear, saturated 1-alkanol, anionic surfactant, and sodium polyacrylate produces a particularly rich, creamy consistency and feel of the whitening and coloring agents according to and preferred present disclosure. Furthermore, this combination guarantees an application-technically optimal viscosity even after mixing with the strongly acidic, aqueous hydrogen peroxide preparation (M2), which leads to a pH value of the ready-to-use application mixture in the range of from about 6.0-8.0, preferably from about 6.5-7.5, in each case measured at 20° C.

Agents preferred and preferentially used as contemplated herein contain, in each case based on the weight of this agent, at least one oil in a total amount of from about 0.01-7% by weight, more preferably from about 0.1-6% by weight, particularly preferably from about 0.5-5.5% by weight, extremely preferably from about 1-5.2% by weight, these amounts including the oils from the optionally contained sodium polyacrylate emulsion preferred as contemplated herein. This additional oil may be selected from the same oils that may be contained in the sodium polyacrylate emulsions preferred by the present disclosure. Preferably at least one additional oil selected from natural and synthetic hydrocarbons, especially preferably mineral oil, paraffin oils, $C_{18}$-$C_{30}$ isoparaffins, especially isoeicosane, polyisobutenes and polydecenes, $C_8$-$C_{16}$ isoparaffins, as well as 1,3-di(2-ethylhexyl)-cyclohexane; branched alkanols containing a hydroxy group and 10 to 50 carbon atoms; the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the above substances. As contemplated herein, particularly preferred oils are selected from paraffin oils, natural oils, especially amaranth seed oil, apricot kernel oil, argan oil, avocado oil, babassu oil, cotton seed oil, borage seed oil, camelina oil, safflower oil, peanut oil, pomegranate kernel oil, grapefruit seed oil, Hemp oil, hazelnut oil, elderberry seed oil, currant seed oil, jojoba oil, linseed oil, macadamia nut oil, maize germ oil, almond oil, marula oil, evening primrose oil, olive oil, palm oil, palm kernel oil, Brazil nut oil, pecan nut oil, peach kernel oil rapeseed oil, castor oil, sea buckthorn pulp oil, sea buckthorn seed oil, Sesame oil, soybean oil, sunflower oil, grape seed oil, walnut oil, wild rose oil, wheat germ oil, and the liquid parts of coconut oil, furthermore synthetic triglyceride oils, especially capric/caprylic triglycerides, also the esters of linear or branched saturated or unsaturated fatty alcohols containing 2-30 carbon atoms with linear or branched saturated or unsaturated fatty acids containing 2-30 carbon atoms which may be hydroxylated, in particular isopropyl palmitate and isopropyl myristate, and mixtures of the above mentioned oils.

Other agents (M1) preferred as contemplated herein and used preferentially as contemplated herein contain at least one polymer selected from cationic and zwitterionic polymers in a total amount of from about 0.1-2% by weight, preferably from about 0.2-1.5% by weight, particularly preferably from about 0.35-0.5% by weight, in each case based on the weight of the agent.

Surprisingly, it was found that the addition of a cationic and zwitterionic polymer in a total amount of from about 0.1-2% by weight further improves the cream gel structure. In addition, the cationic or zwitterionic polymer leads to the fact that even after mixing with an aqueous oxidant composition (M2), a further optimized viscosity is obtained for the application.

Polymers are macromolecules with a molecular weight of at least about 1000 g/mol, preferably of at least about 2500 g/mol, particularly preferably of at least about 5000 g/mol, including identical, repeating organic units. Polymers are produced by polymerization of one type of monomer or by polymerization of different, structurally different types of monomer. If the polymer is produced by polymerizing a type of monomer, it is called a homopolymer. If structurally different monomer types are used in polymerization, experts refer to them as copolymers.

The maximum molecular weight of the polymer depends on the degree of polymerization (number of polymerized monomers) and is co-determined by the polymerization method. For the purposes of the present disclosure, it is preferred that the molecular weight of the zwitterionic polymer is from about 100,000 to about $10^7$ g/mol, preferably from about 200,000 to about $5 \cdot 10^6$ g/mol and particularly preferably from about 500,000 to about $1 \cdot 10^6$ g/mol.

Zwitterionic polymers are those polymers which contain both cationic and anionic groups in the macromolecule. The cationic groups contained in the macromolecule are quaternary ammonium groups. In these quaternary ammonium groups, one positively charged nitrogen atom carries four organic residues. The anionic groupings are —COO— groups or —SO$_3$—groups.

The cationic polymers can be homo- or copolymers or polymers based on natural polymers, where the quaternary nitrogen groups are contained either in the polymer chain or preferably as a substituent on one or more of the monomers. The monomers containing ammonium groups may be copolymerized with non-cationic monomers. Suitable cationic monomers are unsaturated, radically polymerizable compounds which carry at least one cationic group, in particular ammonium-substituted vinyl monomers such as trialkylmethacryloxyalkylammonium, trialkylacryloxyalkylammonium, dialkyldiallylammonium and quaternary vinylammonium monomers with cyclic groups containing cationic nitrogen, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups such as C1 to C7 alkyl groups, especially preferably C1 to C3 alkyl groups.

The monomers containing ammonium groups may be copolymerized with non-cationic monomers. Suitable comonomers are for example acrylamide, methacrylamide; alkyl and dialkyl acrylamide, alkyl and dialkyl methacrylamide, alkyl acrylate, alkyl methacrylate, vinyl caprolactone, vinyl caprolactam, vinyl pyrrolidone, vinyl esters, z. B. vinyl acetate, vinyl alcohol, propylene glycol or ethylene glycol, the alkyl groups of these monomers preferably being C1 to C7 alkyl groups, particularly preferably C1 to C3 alkyl groups.

Preferred cationic and zwitterionic polymers, which have proven to be particularly effective components of inventively preferred combinations of active ingredients, are selected from the group of
Copolymers of dimethyl-diallylammonium salts and acrylic acid, e.g. polyquaternium-22,
Copolymers of dimethyl-diallylammonium salts and methacrylic acid,
Copolymers of N,N,N-trimethyl-3-[(2-methyl-1-oxo-2-propen-1-yl)amino]-1-propanaminium salts and acrylic acid,
Copolymers of N,N,N-trimethyl-3-[(2-methyl-1-oxo-2-propen-1-yl)amino]-1-propanaminium salts and methacrylic acid,
Copolymers of N,N,N-trimethyl-2-[(2-methyl-1-oxo-2-propen-1-yl)amino]-1-ethanaminium salts and acrylic acid,
Copolymers of N,N,N-trimethyl-2-[(2-methyl-1-oxo-2-propen-1-yl)amino]-1-ethanaminium salts and methacrylic acid,
Copolymers of N,N,N-trimethyl-3-[(2-methyl-1-oxo-2-propen-1-yl)amino]-1-propanaminium salts, acrylic acid, and acrylamide, e.g. polyquaternium-53
Copolymers of N,N,N-trimethyl-3-[(2-methyl-1-oxo-2-propen-1-yl)amino]-1-propanaminium salts, methacrylic acid and acrylamide,
Copolymers of 1-ethenyl-3-methyl-1H-imidazolium salts, 1-ethenyl-1H-imidazole, 1-ethenyl-2-pyrrolidinone and methacrylic acid, e.g. polyquaternium-86,
Copolymers of 1-ethenyl-3-methyl-1H-imidazolium salts, 1-ethenyl-1H-imidazole, 1-ethenyl-2-pyrrolidinone and acrylic acid,
Copolymers which contain at least one anionic structural unit of the formula (II) and at least one cationic structural unit of the formula (III)

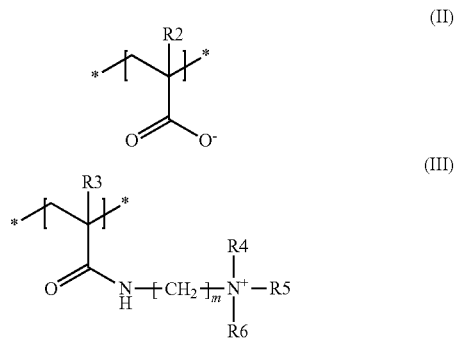

wherein R2 and R3 independently represent a hydrogen atom or a methyl group,
m is an integer from 2 to 6, preferably the numbers 2 or 3, and
the radicals R4, R5 and R6 independently of one another represent a C1-C6 alkyl group, preferably independently of one another a methyl group, an ethyl group or a propyl group, a particularly preferred zwitterionic polymer of this type, prepared according to DE3929973A1, preparation example 1, being known under the INCI name acrylamidopropyltrimonium chloride/acrylate copolymer;
polymeric dimethyldiallylammonium salts and copolymers thereof with esters and amides of acrylic acid and methacrylic acid. Particularly preferred polymers of this type are dimethyldiallylammonium chloride acrylamide copolymers, especially those with the INCI designation Polyquaternium-7. Polyquaternium-7 is for example available as a commercial product Merquat® 550. Another preferred polymer of this type is the homopolymer poly(dimethyldiallylammonium chloride), especially the homopolymers with the INCI designation polyquaternium-6. Polyquaternium-6 is for example available as a commercial product Merquat® 100. Other preferred polymers of this type are terpolymers of dimethyldiallylammonium chloride, acrylamide, and ammonium acrylate, especially those with the INCI designation polyquaternium-39. Polyquaternium-39 is for example available as commercial product Merquat® 3330 and Merquat® 3331. Other preferred polymers of this type are copolymers of dimethyldiallylammonium chloride and acrylic acid, especially those with the INCI designation polyquaternium-22. Polyquaternium-22 is for example available as a commercial product Merquat® 280.
Homopolymers of the general formula —{CH$_2$—[CR$^1$COO—(CH$_2$)$_m$N$^+$R$^2$R$^3$R$^4$]}$_n$ X$^-$, wherein R$^1$=—H or —CH$_3$, R$^2$, R$^3$ and R$^4$ are independently selected from C1-4 alkyl, C1-4 alkenyl or C1-4 hydroxyalkyl groups, m=1, 2, 3 or 4, n is a natural number and X$^-$ is a physiologically acceptable organic or inorganic anion. In the context of these polymers, preference is given to those for which at least one of the following conditions applies: R$^1$ stands for a methyl group, R$^2$, R$^3$ and R$^4$ stand for methyl groups, m has the value 2. Physiologically compatible counter ions X⁻ include halide ions, sulphate ions, phosphate ions, methosulphate ions and organic ions such as lactate, citrate, tartrate and acetate ions. Preferred are methosulphates and halide ions, especially chloride. Other preferably suitable cationic polymers derived from synthetic polymers are, for example, copolymers of A1) from about 0.1 to about 50%, preferably from about 10 to about 50% (based on the total number of monomers in the copolymer) of monomers of formula (IV)

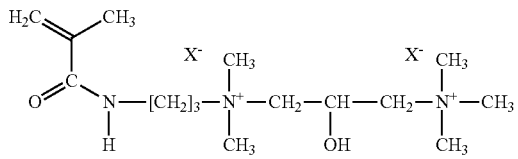

(IV)

in which X stands for chloride, sulphate, methosulphate, and A2) monomers selected from the group including acrylic acid, methacrylic acid and the alkali metal and ammonium salts of these acids, the monomer A2 representing from about 50 to about 99.9%, preferably from about 50 to about 90% (relative to the total number of monomers in the copolymer) of the copolymer.

A highly preferred polymer, which is structured as shown above, is commercially available under the INCI designation Polyquaternium-74.

A particularly suitable homopolymer is poly(methacryloyloxyethyltrimethylammonium chloride) with the INCI designation polyquaternium-37, which is cross-linked if required, and mixtures thereof.

Other agents preferred or preferably used as contemplated herein include at least one polymer selected from cationic and zwitterionic polymers and are present in a total amount of from about 0.1-2% by weight, preferably from about 0.2-1.5% by weight, particularly preferably from about 0.35-0.5% by weight, each based on the weight of the agent.

Further agents which are as contemplated herein particularly preferred or particularly preferably used include at least one cationic or zwitterionic polymer selected from polyquaternium-22, polyquaternium-39, acrylamidopropyltrimonium chloride/acrylate copolymer and polyquaternium-6 as well as mixtures thereof, wherein polyquaternium-22 is extremely preferred, preferably in a total amount of from about 0.1-2 wt. % of the cationic or zwitterionic polymer. %, particularly preferably from about 0.2-1.5 wt. %, extremely preferably from about 0.35-0.5 wt. %, in each case based on the weight of the agent.

A further notable characteristic for the form of the present disclosure as hair dye is the content of at least one oxidation dye precursor as coloring substance.

Oxidation dye precursors can be divided into two categories based on their reaction behavior, so-called developer components, also known as oxidation bases, and coupler components.

Coupler components alone do not form a significant coloration during oxidative dyeing, but always require the presence of developer components. Developer components can form the actual dye with themselves.

Many of the developer and coupler components can be used in free form. For substances with amino groups, however, it may be preferable to use them in salt form, especially in the form of hydrochlorides or hydrobromides or sulphates.

Oxidation dye precursors include developer-type and coupler-type oxidation dye precursors. Particularly suitable developer-type oxidation dye precursors are selected from at least one compound from the group including p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo [1,2-a]pyrazol-1-one and their physiologically tolerable salts. Particularly preferred developer components are selected from p-toluylenediamine, 2-(2-hydroxyethyl)-p-phenylenediamine, N,N-bis-(2-hydroxyethyl)-p-phenylenediamine, 2-methoxymethyl-p-phenylenediamine and/or 4,5-diamino-1-(2-hydroxyethyl)-pyrazole and their physiologically compatible salts and mixtures thereof.

Particularly suitable oxidation dye precursors of the coupler type are selected from the group including 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene (2-amino-4-[(2-hydroxyethyl)amino]-anisole), 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, Resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene 4-Hydroxyindole, 6-Hydroxyindole, 7-Hydroxyindole, 4-hydroxyindoline, 6-Hydroxyindoline, 7-Hydroxyindoline or mixtures of these compounds or their physiologically acceptable salts. Especially preferred coupler components are selected from 3-aminophenol, 5-amino-2-methylphenol, 3-amino-2-chloro-6-methylphenol, 2-hydroxy-4-aminophenoxyethanol, 2-(2,4-diaminophenoxy)ethanol, 1-Methoxy-2-amino-4-(2-hydroxyethylamino)benzene (2-amino-4-[(2-hydroxyethyl)amino]-anisole), resorcinol, 2-methylresorcinol, 4-chlororesorcinol, 2-amino-3-hydroxypyridine, and their physiologically acceptable salts, and mixtures thereof.

In a preferred embodiment, the colorants as contemplated herein contain one or more oxidation dye precursors in a total amount of from about 0.005 to about 12% by weight, preferably from about 0.1 to about 7% by weight, more preferably from about 0.5 to about 5% by weight, more preferably from about 0.7 to about 2.5% by weight and very particularly preferably from about 1 to about 1.8% by weight, based on the weight of the colorant as contemplated herein or the weight of the composition (M1) used as contemplated herein.

In a preferred embodiment, the colorants of the present disclosure contain one or more oxidation dye precursors selected from at least one developer component and optionally at least one coupler component, in a total amount of from about 0.005 to about 12% by weight. %, preferably from about 0.1 to about 7% by weight, more preferably from about 0.5 to about 5% by weight, more preferably from about 0.7 to about 2.5% by weight, and very particularly preferably from about 1 to about 1.8% by weight, based on the weight of the coloring agent as contemplated herein or the weight of the composition (M1) used as contemplated herein.

Based on each individual oxidation dye precursor, it is preferably contained in an amount of from about 0.005-5% by weight, particularly preferably from about 0.01 to 4% by weight, extremely preferably from about 0.1-2% by weight, each based on the weight of the agent.

In a further preferred embodiment of the present disclosure, the agent contains at least one direct dye.

In oxidative hair whiteners and hair dyes for light shades, direct dyes are often used to nuance unwanted reddish tones, which can be caused by melanin degradation products, or to nuance certain blonde shades.

To obtain a balanced and subtle nuance, the present disclosure may also provide that cosmetic products containing OFV additionally contain at least one direct dye.

Direct dyes are dyes that are applied directly to the hair and do not require an oxidative process to develop the color. Direct dyes are usually nitrophenylenediamines, nitroaminophenols, azo dyes, anthraquinones or indophenols.

Direct dyes can be divided into anionic, cationic, and nonionic direct dyes.

Preferred anionic direct dyes are the compounds known under the names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and Tetrabromophenol blue.

Preferred cationic substantive dyes are cationic triphenylmethane dyes, such as Basic Blue 7, Basic Blue 26, Basic Violet 2 and Basic Violet 14, and aromatic systems which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1.4-Diamino-2-nitrobenzene, 2-Amino-4-nitrophenol, 1.4-To-(2-hydroxyethyl)amino-2-nitrobenzene, 3-Nitro-4-(2-hydroxyethyl)aminophenol, 2-(2-Hydroxyethyl)amino-4,6-dinitrophenol, 4-[(2-Hydroxyethyl)amino]-3-nitro-1-methylbenzene, 1-Amino-4-(2-hydroxyethyl)amino-5-chloro-2-nitrobenzene, 4-Amino-3-nitrophenol, 142'-Ureidoethyl)amino-4-nitrobenzene, 2-[(4-Amino-2-nitrophenyl)amino]benzoic acid, 6-Nitro-1,2,3,4-tetrahydroquinoxaline, 2-Hydroxy-1.4-naphthoquinone, picramic acid and its salts, 2-Amino-6-chloro-4-nitrophenol, 4-Ethylamino-3-nitrobenzoic acid and 2-Chloro-6-ethyl-amino-4-nitrophenol.

Furthermore, naturally occurring dyes, such as those contained in henna red, henna neutral, henna black, chamomile flowers, sandalwood, black tea, walnut, rotten bark, sage, blue wood, madder root, catechu and alkanna root can also be used as direct dyes.

Preferably, the cosmetic composition contains at least one direct dye in a total amount of from about 0.001 to about 10% by weight, preferably from about 0.01 to about 8% by weight, preferably from about 0.1 to about 5% by weight, in particular from about 0.5 to about 2% by weight, in each case based on the weight of the cosmetic composition or the composition used as contemplated herein (M1).

Surprisingly, it was found that an addition of 4-hydroxyacetophenone improves the dyeing or brightening result. Other hair whitening or hair dyeing products preferred as contemplated herein are exemplified by the fact that they contain 4-hydroxyacetophenone. Preferably, the cosmetic agent contains from about 0.001 to about 2% by weight, preferably from about 0.01 to about 1% by weight, preferably from about 0.1 to about 0.6% by weight, in particular from about 0.2 to about 0.4% by weight, of 4-hydroxyacetophenone, in each case based on the weight of the cosmetic agent or the composition (M1) used as contemplated herein.

Another object of the present disclosure is a packaging unit (kit-of-parts) which—packed separately—comprises the following:

a) at least one container (C1) containing an agent for oxidative hair coloring which contains, in each case based on its weight:

from about 70-90% by weight, preferably from about 73-86% by weight, particularly preferably from about 76-84% by weight, water, at least one alkalizing agent, at least one crosslinked copolymer composed of acrylic acid and non-ethoxylated esters of acrylic acid with linear C10-C30 monoalcohols as monomers, the crosslinked copolymer being present in a total amount of from about 0.2-0.6% by weight, preferably from about 0.3-0.5% by weight, particularly preferably from about 0.4-0.45% by weight, at least one linear, saturated 1-alkanol with one hydroxy group and 8 to 22 carbon atoms in a total amount of from about 0.3-1.5% by weight, preferably from about 0.4-1.2% by weight, particularly preferably from about 0.5-1.0% by weight, extremely preferably from about 0.6-0.8% by weight, at least one anionic surfactant in a total amount of from about 1-6% by weight, preferably from about 2-5% by weight, and particularly preferably from about 2.5-4.5% by weight, and sodium polyacrylate, preferably with a mass-average molar mass $M_w$ in the range of from about 1,000,000 to about 20,000,000 Daltons, particularly preferably from about 6,000,000 to about 15,000,000 Daltons, preferably in a total amount of from about 0.1-1.5 wt.-%, particularly preferably from about 0.5-1.3% by weight, extremely preferably from about 0.8-1.1% by weight, in each case based on the weight of the agent, the sodium polyacrylate being particularly preferably contained as pregelled in a water-in-oil emulsion, optionally at least one coloring substance selected from oxidation dye precursors, direct-acting hair dyes and mixtures thereof, in which no oxidizing agents are present, and the agent has a pH value in the range from about 7.5 to about 9.5, preferably in the range from about 8.0 to about 9.0, each measured at 20° C., a) at least one container (C2) containing an oxidizing agent preparation (M2), which contains from about 40-96% by weight, preferably from about 70-93% by weight, particularly preferably from about 80-90% by weight, water, furthermore hydrogen peroxide in a total amount of from about 0.5 to about 23% by weight %, more preferably from about 2.5 to about 13%, particularly preferably from about 3 to about 10%, very preferably from about 6 to about 9% by weight, and having a pH value in the range from about 2.0 to about 6.5, preferably from about 2.5-5.5, particularly preferably from about 2.8 to about 5.0, in each case measured at 20° C., wherein optionally at least one copolymer selected from cross-linked acrylic acid/acrylic acid-C1-C6-alkyl ester copolymers and cross-linked methacrylic acid/acrylic acid-C1-C6-alkyl ester copolymers may be contained, preferably in a total amount of from about 0.1-7% by weight, particularly preferably from about 0.5-6% by weight, extremely preferably from about 1-4.5% by weight, where the weight % figures are each based on the weight of the oxidant preparation (M2).

Another subject of the present disclosure is a process for oxidative hair dyeing comprising the following process steps:

i) Provision of a cosmetic composition (M1) for oxidative hair dyeing of keratinous fibers, comprising from about 70-90% by weight, preferably from about 73-86% by weight, particularly preferably from about 76-84% by weight, water, at least one alkalizing agent, at least one crosslinked copolymer composed of acrylic acid and non-ethoxylated esters of acrylic acid with linear C10-C30 monoalcohols as monomers, the cross-linked copolymer being present in a total amount of from about 0.2-0.6% by weight, preferably from about 0.3-0.5% by weight, particularly preferably from about 0.4-0.45% by weight, at least one linear, saturated 1-alkanol with one hydroxy group and 8 to 22 carbon atoms in a total amount of from about 0.3-1.5% by weight, preferably from about 0.4-1.2% by weight, particularly preferably from about 0.5-1.0% by weight, extremely preferably from about 0.6-0.8% by weight, at least one anionic surfactant in a total amount of from about 1-6% by weight, preferably from about 2-5% by weight, and particularly preferably from about 2.5-4.5% by weight, and sodium polyacrylate, preferably with a mass-average molar mass $M_w$ in the range of from about 1,000,000 to about 20,000,000 Daltons, particularly preferably from about 6,000,000 to about 15,000,000 Daltons, preferably in a total amount of from about 0.1-1.5 wt.-%, particularly preferably from about 0.5-1.3% by weight, extremely preferably from about 0.8-1.1% by weight, in each case based on the weight of the agent, the sodium polyacrylate being particularly preferably contained as pregelled in a water-in-oil emulsion, optionally at least one coloring substance selected from oxidation dye precursors, direct-acting hair dyes and mixtures thereof, in which no oxidizing agents are present, and the agent has a pH value in the range from about 7.5 to about 9.5, preferably in the range from about 8.0 to about 9.0, each measured at 20° C., ii) Providing an oxidizing agent preparation (M2) containing from about 40-96 wt. %, preferably from about 70-93 wt. %, more preferably from about 80-90 wt. %, water, further hydrogen peroxide in a total amount of from about 0.5 to about 23 wt. %, preferably from about 70-93 wt. %, more preferably from about 80-90 wt. %, water, further hydrogen peroxide in a total amount of from about 0.5 to about 23 wt. %, preferably from about 2.5-13 wt. %, more preferably from about 3-10 wt. %, particularly preferably from about 6 to about 9 wt. % and having a pH value in the range from about 2.0 to about 6.5, preferably from about 2.5-5.5, particularly preferably from about 2.8 to about 5.0, in each case measured at 20° C., wherein optionally at least one copolymer selected from cross-linked acrylic acid/acrylic acid-C1-C6-alkyl ester copolymers and cross-linked methacrylic acid/acrylic acid-C1-C6-alkyl ester copolymers may be contained, preferably in a total amount of from about 0.1-7 wt. %, particularly preferably from about 0.5-6 wt. %, extremely preferably from about 1-4.5 wt. %, in each case based on the weight of the oxidant preparation (M2), iii) Mixing of the cosmetic agent (M1) with the oxidizing agent preparation (M2), preferably in a weight ratio (M1):(M2) in the range of from about 0.2:1:to about 3:1, preferably from about 0.3:1 to about 2.5:1, particularly preferably from about 1:1 to about 1.5:1, immediately afterwards iv) Apply the mixture obtained in step iii) to the hair and leave this mixture on the hair for a period of from about 1 to about 60 minutes, preferably from about 20 to about 45 minutes, at room temperature and/or at from about 30-60° C., v) rinsing the hair with water and/or a cleansing composition, and vi) if necessary, apply an after-treatment agent to the hair and rinse if necessary, then dry, the application mixture of (M1) and (M2) has a pH value in the range of from about 6.0-8.0, preferably in the range of from about 6.5-7.5, each measured at 20° C.

For oxidative hair whitening or hair dyeing processes, the composition (M1) as contemplated herein, which optionally contains one or more oxidation dye precursors and optionally one or more direct dyes, is usually mixed with an aqueous composition (M2) containing an oxidizing agent to form a ready-to-use whitening or dyeing mixture immediately before application to the hair and then applied to the hair. In most cases, the agent (M1) of the present disclosure and the oxidant-containing composition (M2) are matched to one another in such a way that, at a mixing ratio of about 1 to 1, based on parts by weight, an initial concentration of hydrogen peroxide of from about 0.5-12% by weight, preferably from about 0.9-7% by weight, particularly preferably from about 1.5-5% by weight, exceptionally from about 2.5-4% by weight of hydrogen peroxide (calculated as about 100% $H_2O_2$), in each case based on the weight of the application mixture, is present in the finished application mixture. However, it is just as well possible to match the agent of the present disclosure (M1) and the oxidant-containing composition (M2) in such a way that the concentrations required in the oxidation colorant ready for use (application mixture), as indicated above, are obtained by mixing ratios other than about 1:1, for example by a weight-based mixing ratio of about 5:2 or about 1:2 or about 1:3 or even about 2:3 or about 3:1.

As contemplated herein, preferred weight-related mixing ratios (M1):(M2) are in the range from about 0.2:1:to about 3:1, preferably from about 0.3:1 to about 2.5:1, particularly preferably from about 1:1 to about 1.5:1.

Oxidative hair brightening or hair dyeing kits as contemplated herein include the finished application mixture of (M1) and (M2) with a pH value in the range of from about 6.0-8.0, preferably in the range of from about 6.5-7.5, each measured at 20° C.

As contemplated herein, the term "room temperature" refers to the temperature in the room in which a person usually uses a hair whitening or coloring product, i.e. usually a bathroom or hairdressing salon, where the temperature is in the range about 10-29° C.

Leaving the hair brightening or hair coloring application mixture in process step iv) in the hair brightening or hair coloring processes as contemplated herein or preferred as contemplated herein can also take place at at least about 30° C., preferably at from about 30-60° C., particularly preferably at from about 32-50° C., if the hair is heated e.g. with a heating bonnet or with a radiant heater.

The oxidizing agent preparation (M2) used in dyeing kits as contemplated herein and preferred present disclosure and in dyeing processes as contemplated herein and preferred present disclosure contains, in each case based on its weight, from about 40-96% by weight, preferably from about 70-93% by weight, particularly preferably from about 80-90% by weight, of water.

The oxidizing agent preparation (M2) used in dyeing kits as contemplated herein and preferred present disclosure and in dyeing processes as contemplated herein and preferred present disclosure further contains, in each case based on its weight, from about 0.5 to about 23% by weight, more preferably from about 2.5 to about 13% by weight, particularly preferably from about 3 to about 10% by weight, very particularly preferably from about 6 to about 9% by weight of hydrogen peroxide.

To stabilize the hydrogen peroxide, the oxidant preparation (M2) has a pH value in the range of from about 2.0 to about 6.5, preferably from about 2.5-5.5, particularly preferably from about 2.8 to about 5.0, each measured at 20° C.

The viscosity of agents (M1) preferred as contemplated herein, which is in the range of from about 3000-25,000 mPas, preferably from about 4,000-20,000 mPas, particularly preferably from about 6,000-12,000 mPas, each measured at 20° C. with a Haake VT 550 viscometer, measuring system SV, is excellently suited for the handling of this agent itself (production, filling, dosing to produce the mixture with the oxidant preparation). The oxidant preparation (M2) usually has a low viscosity in the range of from about 10-6000 mPas, preferably from about 200-5000 mPas, especially preferably from about 1000-4500 mPas, each measured at 20° C. For application to the hair, however, the application mixture should have a significantly higher viscosity so that it remains on the hair during the entire application time (in the range of from about 5-60 minutes, preferably from about 30-45 minutes) and does not drip down. A distinction is made between whether the application mixture is prepared by shaking both compositions (M1) and (M2) in an application bottle, from which the application mixture is applied to the hair immediately after mixing with the aid of an application spout as a bottle top (bottle application), or whether the application mixture is prepared by mixing both compositions (M1) and (M2) in a bowl, from which the application mixture is applied to the hair with a brush immediately after mixing (brush application). The bottle application is particularly suitable for colorants that are sold in retail outlets with a recommendation for use by the consumer himself. The brush application is especially suitable for whitening and coloring products, which are produced in the hairdressing salon by the hairdresser and applied to the consumer's hair.

Surprisingly, it was found that an application mixture with a viscosity particularly suitable for bottle application is obtained by mixing the agent (M1) as contemplated herein or preferred present disclosure with an oxidizing agent preparation (M2) containing at least one niotenside in a total amount of from about 0.05-2 wt. %, preferably from about 0.3-1.5 wt. %, furthermore at least one linear, saturated 1-alkanol with 14 to 22 carbon atoms, selected from 1-tetradecanol (myristyl alcohol), 1-hexadecanol (cetyl alcohol), 1-octadecanol (stearyl alcohol), 1-eicosanol (arachyl alcohol) and 1-docosanol (behenyl alcohol) as well as mixtures thereof, in a total amount of from about 1-5% by weight. % by weight, preferably from about 1.5-4% by weight, and further contains at least one oil in a total amount of from about 0.2-10% by weight, preferably from about 1-5% by weight, particularly preferably from about 2-4% by weight, all quantities being based on the weight of the oxidant preparation (M2).

It is particularly preferred that this oxidant preparation (M2) does not contain a cationic surfactant or a polymer with a degree of polymerization of at least about 200 or a polymer with a molecular weight of about 10,000 daltons or higher.

The non-ionic surfactants used in the oxidizing agent preparations (M2) used as contemplated herein are selected from the same surfactants from which the niotensides contained in the agents (M1) used as contemplated herein and those used as contemplated herein are selected.

For the purposes of the present application, the above-mentioned linear, saturated 1-alkanols with one hydroxy group are not considered to be surfactants, even regarding oxidizing preparations (M2).

The at least one oil present in the oxidant preparation (M2) in a total amount of from about 0.2-10% by weight, preferably from about 1-5% by weight, particularly preferably from about 2-4% by weight %, in each case based on the weight of the preparation (M2), is preferably selected from natural and synthetic hydrocarbons, particularly preferably mineral oil, paraffin oils, $C_{18}$-$C_{30}$ isoparaffins, in particular isoeicosane, polyisobutenes and polydecenes, $C_8$-$C_{16}$ isoparaffins, and 1,3-di(2-ethylhexyl)cyclohexane; branched alkanols containing a hydroxy group and 10 to 50 carbon atoms; the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$-alkanols; the $C_5$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the above substances. Oils particularly preferred in this connection as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from paraffin oil, isopropyl palmitate and isopropyl myristate and mixtures thereof.

Mixing the agent as contemplated herein or preferred present disclosure with such an oxidizing agent preparation (M2) leads to the desired application viscosity and thus to optimal application properties. The application mixtures obtained in this way, especially with weight-related mixing ratios (M1):(M2) in the range from about 0.2:1:to about 3:1, preferably from about 0.3:1 to about 2.5:1, particularly preferably from about 1:1 to about 1.5:1, preferably have a viscosity in the range of from about 3,000-30,000 mPas, preferably from about 4,000-20,000 mPas, particularly preferably from about 7,000-10,000 mPas, each measured at 20° C. (Haake VT 550 rotational viscometer, measuring system MV II).

A further packaging unit (kit-of-parts) preferred as contemplated herein includes the oxidizing agent preparation (M2) that contains at least one niotenside in a total amount of from about 0.05-2 wt. %, preferably from about 0.3-1.5 wt. %, furthermore at least one linear, saturated 1-alkanol with 14 to 22 carbon atoms, selected from 1-tetradecanol (myristyl alcohol), 1-hexadecanol (cetyl alcohol), 1-octadecanol (stearyl alcohol), 1-eicosanol (arachyl alcohol) and 1-docosanol (behenyl alcohol) as well as mixtures thereof, in a total amount of from about 1-5 wt. %, preferably from about 1.5-4 wt. % and further contains at least one oil in a total amount of from about 0.2-10% by weight, preferably from about 1-5% by weight, particularly preferably from about 2-4% by weight, wherein all quantity data refer to the weight of the oxidant preparation (M2) and wherein it is particularly preferred that this oxidant preparation (M2) does not contain a cationic surfactant and no polymer with a degree of polymerization of at least about 200 and no polymer with a molecular weight of about 10,000 Dalton or higher.

In another embodiment of the present disclosure, it may be preferred to mix the agent (M1) as contemplated herein or preferred present disclosure with an oxidizing agent preparation (M2) containing at least one copolymer selected from cross-linked acrylic acid/acrylic acid-C1-C6-alkyl ester copolymers and cross-linked methacrylic acid/acrylic acid-C1-C6-alkyl ester copolymers, preferably in a total amount of from about 0.1-7 wt. %. % by weight, particularly preferably from about 0.5-6% by weight, extremely preferably from about 1-4.5% by weight, in each case based on the weight of the oxidizing agent preparation (M2). Mixing the agent as contemplated herein or preferred present disclosure with such an oxidizing agent preparation (M2) leads to the desired application viscosity and thus to optimal application properties. The application mixtures obtained in this way, especially with weight-related mixing ratios (M1):(M2) in the range from about 0.2:1:to about 3:1, preferably from about 0.3:1 to about 2.5:1, particularly preferably from about 1:1 to about 1.5:1, preferably have a viscosity in the range of from about 3.000-30,000 mPas, preferably from about 4,000-20,000 mPas, particularly preferably from about 7,000-10,000 mPas, each measured at 20° C. (Haake VT 550 rotational viscometer, measuring system MV II).

A further packaging unit (kit-of-parts) preferred as contemplated herein includes the oxidizing agent preparation (M2) that contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7 wt.-%. %, particularly preferably from about 0.5-6% by weight, extremely preferably from about 1-4.5% by weight, in each case based on the weight of the oxidizing agent preparation (M2), and preferably contains no cationic surfactant.

A further process for oxidative hair whitening or hair coloring preferred as contemplated herein is exemplified in that the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7 wt.-%. %, particularly preferably from about 0.5-6% by weight, extremely preferably from about 1-4.5% by weight, in each case based on the weight of the oxidizing agent preparation (M2), and preferably contains no cationic surfactant.

Preferred cross-linked copolymers of this type are selected from—each cross-linked—methacrylic acid/methyl acrylate, methacrylic acid/ethyl acrylate, methacrylic acid/propyl acrylate, methacrylic acid/butyl acrylate, methacrylic acid/pentyl acrylate, Methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof.

A further packaging unit (kit-of-parts) preferred as contemplated herein is exemplified in that the oxidizing agent preparation (M2) contains at least one cross-linked copolymer selected from—in each case cross-linked—methacrylic acid/methyl acrylate, methacrylic acid/ethyl acrylate, methacrylic acid/propyl acrylate, Methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of from about 0.1-7 wt.-%, particularly preferably from about 0.5-6 wt. %, extremely preferably from about 1-4.5 wt. %, each based on the weight of the oxidant preparation (M2), and contains no cationic surfactant.

Another preferred method as contemplated herein for oxidative hair lightening or hair coloring is exemplified in that the oxidizing agent preparation (M2) comprises at least one crosslinked copolymer, selected from—in each case crosslinked—methacrylic acid/methyl acrylate, methacrylic acid/ethyl acrylate, methacrylic acid/propyl acrylate, methacrylic acid/butyl acrylate, Methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of from about 0, 1-7% by weight, particularly preferably from about 0.5-6% by weight, extremely preferably from about 1-4.5% by weight, in each case based on the weight of the oxidizing agent preparation (M2), and contains no cationic surfactant.

The oxidizing agent preparation (M2) used in other whitening or dyeing kits preferred as contemplated herein and in whitening or dyeing processes preferred as contemplated herein contains at least one surfactant selected from anionic surfactants and nonionic surfactants and mixtures thereof in a total amount of from about 0.05-2 wt. %, preferably from about 0.3-1.5 wt. %. and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol), 1-eicosanol (arachyl alcohol) and 1-docosanol and mixtures thereof, in a total amount of from about 1-5% by weight. % by weight, preferably from about 1.5-4% by weight, all quantities being based on the weight of the oxidant preparation (M2).

The anionic surfactants and the non-ionic surfactants used in the oxidizing preparations (M2) used as contemplated herein are selected from the same surfactants from which the anionic and non-ionic surfactants contained in the preparations (M1) used as contemplated herein and the preparations used as contemplated herein are selected.

For the purposes of the present application, the abovementioned linear, saturated 1-alkanols with one hydroxy group are not considered to be surfactants, even regarding oxidizing preparations (M2).

In a further preferred embodiment of the present disclosure, the oxidizing agent preparation (M2) used as contemplated herein contains at least one oil in a total amount of from about 0.2-50% by weight, preferably from about 2-40% by weight, particularly preferably from about 8-30% by weight, extremely preferably from about 15-25% by weight, in each case based on the weight of the oxidizing agent preparation (M2).

The at least one oil present in the oxidant preparation (M2) in a total amount of 0.2-50% by weight, preferably 2-40% by weight, particularly preferably 8-30% by weight, extremely preferably 15-25% by weight, in each case based on the weight of the preparation (M2), is preferably selected from natural and synthetic hydrocarbons, particularly preferably from mineral oil, paraffin oils, $C_{18}$-$C_{30}$ isoparaffins, in particular isoeicosan, polyisobutenes and polydecenes, $C_8$-$C_{16}$ isoparaffins, and 1,3-di(2-ethylhexyl)cyclohexane; branched alkanols containing a hydroxy group and 10 to 50 carbon atoms; the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the above substances. Oils particularly preferred in this connection as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from paraffin oil, isopropyl palmitate and isopropyl myristate and mixtures thereof.

A further packaging unit preferred as contemplated herein (kit-of-parts) and a further hair brightening or hair dyeing process preferred as contemplated herein are exemplified in that the oxidizing agent preparation (M2) contains at least one oil in a total amount of from about 0.2-50% by weight, preferably from about 2-40% by weight, particularly preferably from about 8-30% by weight, extremely preferably from about 15-25% by weight, in each case based on the weight of the oxidizing agent preparation (M2), but no cationic surfactant.

A further packaging unit preferred as contemplated herein (kit-of-parts) and a further hair whitening or hair dyeing process preferred as contemplated herein are exemplified in that the oxidizing agent preparation (M2) contains at least one oil in a total amount of from about 0.2-50% by weight, preferably from about 2-40% by weight. % by weight, particularly preferably from about 8-30% by weight, extremely preferably from about 15-25% by weight, in each case based on the weight of the oxidant preparation (M2), but does not contain a polymer with a degree of polymerization of at least about 200 and no polymer with a molecular weight of about 10,000 daltons or higher.

A further packaging unit preferred as contemplated herein (kit-of-parts) and a further hair whitening or hair dyeing process preferred as contemplated herein are exemplified in that the oxidizing agent preparation (M2) contains at least one oil in a total amount of from about 0.2-50% by weight, preferably from about 2-40% by weight. % by weight, particularly preferably from about 8-30% by weight, extremely preferably from about 15-25% by weight, in each case based on the weight of the oxidant preparation (M2), but contains no cationic surfactant, no polymer with a degree of polymerization of at least about 200 and no polymer with a molecular weight of about 10,000 daltons or higher.

In another preferred embodiment of the present disclosure, it was found that an application mixture with a viscosity particularly suitable for brush application is obtained by mixing the agent (M1) as contemplated herein or preferred present disclosure with an oxidizing agent preparation (M2) containing at least one cationic surfactant. During mixing, the interaction between the at least one crosslinked copolymer of acrylic acid and non-ethoxylated esters of acrylic acid with linear C10-C30 monoalcohols and the at least one cationic surfactant leads to the desired increase in viscosity. The resulting consistency of the application mixture leads to optimal application properties.

In a further preferred embodiment of the present disclosure, the oxidant preparation (M2) used as contemplated herein contains at least one cationic surfactant, preferably in a total amount of from about 0.05-3% by weight, particularly preferably of from about 0.1-1.5% by weight, extremely preferably of from about 0.3-0.9% by weight, in each case based on the weight of the oxidant preparation (M2).

Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually including a hydrocarbon backbone (e.g. including one or two linear or branched alkyl chains) and the positive charge(s) being located in the hydrophilic head group. Cationic surfactants adsorb at interfaces and aggregate in aqueous solution above the critical micelle formation concentration to form positively charged micelles.

As contemplated herein, cationic surfactants of the type of quaternary ammonium compounds, esterquats and alkylamidoamines are preferred. Preferred quaternary ammonium compounds are ammonium halides, such as alkyltrimethylammonium chlorides, dialkyldimethylammonium chlorides, trialkylmethylammonium chlorides, as well as the imidazolium compounds known under the INCI designations Quaternium-27 and Quaternium -83. Other preferred quaternary ammonium compounds are tetraalkylammonium salts, such as in particular the one known under the INCI designation Quaternium-52, a poly(oxy-1,2-ethanediyl), ((octadecylnitrilio)tri-2,1-ethanediyl)tris(hydroxy)phosphate (1:1) salt, which has the general structural formula (III), wherein x+y+z=10:

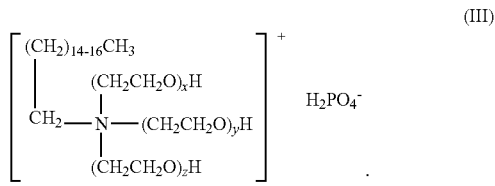

The long alkyl chains of the surfactants mentioned above preferably have 10 to 22, particularly preferably 12 to 18 carbon atoms. Behenyl trimethylammonium chloride, stearyl trimethylammonium chloride and cetyl trimethylammonium chloride are particularly preferred, with stearyl trimethylammonium chloride being extremely preferred. Further cationic surfactants suitable as contemplated herein are quaternized protein hydrolysates. Alkylamidoamines are usually produced by amidation of natural or synthetic fatty acids and fatty acid cuts with dialkylaminoamines Tego-amid® S 18 (stearamidopropyldimethylamine) is a suitable compound from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1.2-dihydroxypropyl dialkylamines. Such products are sold under the Stepantex, Dehyquart and Armocare trademarks.

C10-C22-alkyl trimethyl ammonium chlorides have proven to be particularly suitable in terms of optimum application properties and optimum brightening or dyeing results. Particularly preferred oxidizing agent preparations (M2) used as contemplated herein include at least one cationic surfactant in a total amount of from about 0.05-3% by weight, particularly preferably from about 0.1-1.5% by weight from about 0.3 to about 0.9% by weight, based in each case on the weight of the oxidizing agent preparation (M2), preferably at least one surfactant selected from C10-C22-alkyltrimethylammonium chlorides, in particular selected from behenyltrimethylammonium chloride, stearyltrimethylammonium chloride and cetyltrimethylammonium chloride, and mixtures of these surfactants. Extremely preferred oxidant preparations (M2) used as contemplated herein contain stearyl trimethylammonium chloride in a total amount of from about 0.05-3 wt. %, particularly preferably from about 0.1-1.5 wt. %, extremely preferably from about 0.3-0.9 wt. %, each based on the weight of the oxidant preparation (M2).

A further packaging unit preferred as contemplated herein (kit-of-parts) and a further hair brightening or hair dyeing process preferred as contemplated herein are exemplified in that the oxidizing agent preparation (M2) contains at least one cationic surfactant, preferably in a total amount of from about 0.05-3% by weight, particularly preferably of from about 0.1-1.5% by weight, extremely preferably of from about 0.3-0.9% by weight, in each case based on the weight of the oxidizing agent preparation (M2).

A further packaging unit preferred as contemplated herein (kit-of-parts) and a further hair whitening or hair dyeing process preferred as contemplated herein are exemplified in that the oxidizing agent preparation (M2) contains at least one cationic surfactant, preferably in a total amount of from about 0.05-3 wt. %, particularly preferably from about 0.1-1.5% by weight, extremely preferably from about 0.3-0.9% by weight, in each case based on the weight of the oxidizing agent preparation (M2), but does not contain any polymer with a degree of polymerization of at least about 200 and no polymer with a molecular weight of about 10,000 daltons or higher.

It was found that the thickening through the interaction between the copolymer in the agent of the present disclosure and the cationic surfactant in the oxidizer preparation (M2) is sufficient and cannot be further increased or even impaired in its application properties by the presence of a polymer with a degree of polymerization of at least about 200 or a polymer with a molecular weight of about 10,000 daltons or higher.

A further packaging unit preferred as contemplated herein (kit-of-parts) and a further hair whitening or hair dyeing process preferred as contemplated herein are exemplified in that the oxidizing agent preparation (M2) contains at least one surfactant selected from anionic surfactants and nonionic surfactants and mixtures thereof in a total amount of from about 0.05-2% by weight, preferably from about 0.3-1.5% by weight and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight, preferably from about 1.5-4% by weight, in each case based on the weight of the oxidant preparation (M2).

A further packaging unit preferred as contemplated herein (kit-of-parts) and a further hair whitening or hair dyeing process preferred as contemplated herein are exemplified in that the oxidizing agent preparation (M2) contains at least one surfactant selected from anionic surfactants and nonionic surfactants and mixtures thereof in a total amount of from about 0.05-2% by weight, preferably from about 0.3-1.5% by weight. and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol), 1-eicosanol (arachyl alcohol) and 1-docosanol and mixtures thereof, in a total amount of from about 1-5% by weight. %, preferably from about 1.5-4% by weight, each based on the weight of the oxidant preparation (M2), but does not contain a polymer with a degree of polymerization of at least about 200 and no polymer with a molecular weight of about 10,000 daltons or higher.

It was found that the thickening through the interaction between the copolymer in the agent of the present disclosure and the aforementioned surfactant/1-alkanol mixture in the oxidizer preparation (M2) is sufficient and cannot be further increased or even impaired in its application properties by the presence of a polymer with a degree of polymerization of at least about 200 or a polymer with a molecular weight of about 10,000 daltons or higher.

A further packaging unit preferred as contemplated herein (kit-of-parts) and a further hair whitening or hair dyeing process preferred as contemplated herein are exemplified in that the oxidizing agent preparation (M2) contains at least one surfactant selected from anionic surfactants and nonionic surfactants and mixtures thereof in a total amount of from about 0.05-2% by weight, preferably from about 0.3-1.5% by weight. at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight. %, preferably from about 1.5-4% by weight, and at least one oil in a total amount of from about 0.2-50% by weight, preferably from about 2-40% by weight, particularly preferably from about 8-30% by weight, extremely preferably from about 15-25% by weight, in each case based on the weight of the oxidant preparation (M2).

A further packaging unit preferred as contemplated herein (kit-of-parts) and a further hair whitening or hair dyeing process preferred as contemplated herein are exemplified in that the oxidizing agent preparation (M2) contains at least one surfactant selected from anionic surfactants and non-ionic surfactants and mixtures thereof in a total amount of from about 0.05-2 wt. %, preferably from about 0.3-1.5% by weight, at least one linear, saturated 1-alkanol with 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight, preferably from about 1.5-4% by weight, and at least one oil in a total amount of from about 0.2-50% by weight, preferably from about 2-40% by weight, particularly preferably from about 8-30% by weight, extremely preferably from about 15-25% by weight, in each case based on the weight of the oxidant preparation (M2), but does not contain a polymer with a degree of polymerization of at least about 200 and no polymer with a molecular weight of about 10,000 daltons or higher.

The oxidizing agent preparations (M2) used as contemplated herein and preferably used as contemplated herein may also contain stabilizers, especially complexing agents, and pH buffer substances.

With respect to the cosmetic agent (M1) in container C1 and the oxidizing agent preparation (M2) in container C2 of the Present disclosureal and Preferred Present disclosureal Kits, what has been said about the Present disclosureal and Preferred Present disclosureal Cosmetics applies mutatis mutandis.

With respect to the cosmetic product (M1) in container C1 of the oxidative hair lightening or hair coloring process as contemplated herein and preferred present disclosure, what has been said about the cosmetic products as contemplated herein and preferred present disclosure applies mutatis mutandis.

With respect to the oxidizing agent preparation (M2) in container C2 of the oxidative hair lightening or hair coloring process as contemplated herein and preferred present disclosure, the same applies mutatis mutandis to the oxidizing agent preparations (M2) of the oxidative hair lightening or hair coloring kits as contemplated herein and preferred present disclosure.

The walls of containers C1 and C2 are preferably made of a polyolefin, such as polypropylene (PP), high density polyethylene (HDPE), medium density polyethylene (MDPE), low density polyethylene (LDPE), linear low-density polyethylene (LLDPE). Among these, polyethylene, especially high-density polyethylene (HDPE), is preferred.

For improved mixing of (M1) and (M2), it is preferred that the container (C2) containing the oxidant preparation (M2) is designed as a bottle and has a reclosable opening, such as a snap-on or screw cap. This makes it easier to add the color-changing agent from container (C1), which in turn is preferably in the form of a polyolefin bottle.

In summary, the subject matter of the present disclosure is summarized in the following points:
1. Agent for oxidative hair lightening or hair coloring, containing, in each case based on the weight of the agent,
    from about 70-90% by weight, preferably from about 73-86% by weight, particularly preferably from about 76-84% by weight, water,
    at least one alkalizing agent,
    at least one crosslinked copolymer composed of acrylic acid and non-ethoxylated esters of acrylic acid with linear C10-C30 monoalcohols as monomers, the crosslinked copolymer being present in a total amount of from about 0.2-0.6% by weight, preferably from about 0.3-0.5% by weight, particularly preferably from about 0.4-0.45% by weight, in each case based on the weight of the agent,
    at least one linear, saturated 1-alkanol with one hydroxy group and 8 to 22 carbon atoms in a total amount of from about 0.3-1.5% by weight, preferably from about 0.4-1.2% by weight, particularly preferably from about 0.5-1.0% by weight, extremely preferably from about 0.6-0.8% by weight,
    at least one anionic surfactant in a total amount of from about 1-6% by weight, preferably from about 2-5% by weight, and particularly preferably from about 2.5-4.5% by weight, and
    at least one polymer selected from cationic and zwitterionic polymers in a total amount of from about 0.1-2% by weight, preferably from about 0.2-1.5% by weight, more preferably from about 0.35-0.5% by weight,
    optionally at least one coloring substance selected from oxidation dye precursors, direct-acting hair dyes and mixtures thereof, whereby no oxidizing agents are contained,
    sodium polyacrylate, preferably with a mass-average molar mass $M_w$ in the range of about 1,000,000 to about 20,000,000 Daltons, particularly preferably from about 6,000,000 to about 15,000,000 Daltons, preferably in a total amount of from about 0.1-1.5 wt.-%, particularly preferably from about 0.5-1.3% by weight, extremely preferably from about 0.8-1.1% by weight, in each case based on the weight of the agent, the sodium polyacrylate being particularly preferably contained as pregelled in a water-in-oil emulsion,
    wherein the agent has a pH value in the range from about 7.5 to about 9.5, preferably in the range from about 8.0 to about 9.0, each measured at 20° C.
2. Agent according to point 1, wherein the alkalizing agent is selected from the group comprising ammonium hydroxide, basic amino acids, alkali hydroxides, alkanolamines, alkali metal metasilicates, alkali phosphates and alkali hydrogen phosphates and mixtures thereof, particularly preferably selected from the group comprising alkanolamines, potassium hydroxide, sodium hydroxide and mixtures thereof.
3. Agent according to point 1 or 2, wherein the at least one anionic surfactant is selected from $C_8$-$C_{20}$ alkyl sulphates, $C_8$-$C_{20}$ alkyl ether sulphates and $C_8$-$C_{20}$ ether carboxylic acids, in each case with 8 to 20 C atoms in the alkyl group and 0 to 12 ethylene oxide groups in the molecule, sodium laureth sulphate with 1 to 3, particularly preferably 2, ethylene oxide groups in the molecule being preferably present.
4. Agent according to one of the points 1-3, wherein the at least one crosslinked copolymer of acrylic acid and non-ethoxylated esters of acrylic acid with linear C10-C30 monoalcohols is selected from copolymers with the INCI designation acrylates/C10-30 alkyl acrylates crosspolymer.

5. Agent according to one of the points 1-4, wherein a viscosity in the range of from about 3,000-25,000 mPas, preferably from about 4,000-20,000 mPas, particularly preferably from about 7,000-10,000 mPas, each measured at 20° C. with a Haake VT 550 rotational viscometer, measuring system SV.

6. Agent according to one of the points 1-5, wherein the at least one nonionic surfactant is selected from among those which are treated with 7-80 mol ethylene oxide per mol ethoxylated castor oil, ethoxylated $C_8$-$C_{30}$ alkanols with 6-30, preferably 12 to 20 mol ethylene oxide per mol, ethoxylated $C_8$-$C_{30}$ carboxylic acids with 5-30 mol ethylene oxide per mol with 4-50 mol ethylene oxide per mol ethoxylated sorbitan monoesters of linear saturated and unsaturated $C_{12}$-$C_{30}$ carboxylic acids which may be hydroxylated, alkyl mono- and -oligoglycosides having 8 to 22 carbon atoms in the alkyl radical, and mixtures of the above mentioned substances.

7. Agent according to one of the points 1-6, wherein at least one oil, preferably in a total amount of from about 0.01-7% by weight, more preferably from about 0.1-6% by weight, particularly preferably from about 0.5-5.5% by weight, extremely preferably from about 1-5.2% by weight, each based on the weight of the agent.

8. Agent according to one of the points 1-7, wherein the at least one linear, saturated 1-alkanol with one hydroxy group and 8 to 22 carbon atoms is selected from lauryl alcohol, coconut alcohol, 1-tetradecanol (myristyl alcohol), cetyl alcohol and stearyl alcohol as well as mixtures thereof, in particular from coconut alcohol and lauryl alcohol.

9. Agent according to one of the points 1-8, wherein the at least one nonionic surfactant is contained in a total amount of from about 0.01-1% by weight, preferably from about 0.05-0.5% by weight, and particularly preferably from about 0.1-0.3% by weight, each based on the weight of the agent.

10. Agent according to one of points 1-9, wherein the at least one oil is selected from natural and synthetic hydrocarbons, particularly preferably from mineral oil, paraffin oils, $C_{18}$-$C_{30}$ isoparaffins, in particular isoeicosane, polyisobutenes and polydecenes, $C_8$-$C_{16}$ isoparaffins, and 1,3-di(2-ethylhexyl)-cyclohexane; branched alkanols containing a hydroxy group and 10 to 50 carbon atoms, the benzoic acid esters of linear or branched $C_{8-22}$ alkanols; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the above substances.

11. The agent according to one of the points 1-10, wherein at least one coloring substance selected from oxidation dye precursors is contained, preferably in an amount of from about 0.005-5% by weight, based on the weight of the agent, particularly preferably at least one developer component and optionally at least one coupler component is contained, wherein extremely preferably the total amount of oxidation dye precursors is from about 0.005-12% by weight, preferably from about 0.1-7% by weight, particularly preferably from about 0.5-5% by weight, each based on the weight of the agent.

12. The agent according to one of the points 1-11, wherein at least one coloring substance selected from direct-acting hair dyes, preferably in a total amount of from about 0.001 to about 10% by weight, preferably of from about 0.01 to about 8% by weight, more preferably of from about 0.1 to about 5% by weight, in particular of from about 0.5 to about 2% by weight, each based on the weight of the agent.

13. The agent according to one of the points 1-12, wherein at least one polymer selected from cationic and zwitterionic polymers is contained in a total amount of from about 0.1-2% by weight, preferably from about 0.2-1.5% by weight, particularly preferably from about 0.35-0.5% by weight, each based on the weight of the agent.

14. The agent according to one of the points 1-13, wherein the at least one cationic or zwitterionic polymer is selected from polyquaternium-22, polyquaternium-39, Acrylamidopropyltrimonium chloride/acrylate copolymer and polyquaternium-6 and mixtures thereof, polyquaternium-22 being particularly preferred.

15. The agent according to one of the points 1-14, wherein polyquaternium-22 is contained, preferably in an amount of from about 0.1-2% by weight, particularly preferably from about 0.2-1.5% by weight, extremely preferably from about 0.35-0.5% by weight, each based on the weight of the agent.

16. The agent according to one of the points 1-15, wherein 4-hydroxyacetophenone, preferably in an amount of from about 0.001 to about 2% by weight, preferably of from about 0.01 to about 1% by weight, preferably of from about 0.1 to about 0.6% by weight, in particular of from about 0.2 to about 0.4% by weight, each based on the weight of the agent.

17. Kit-of-parts packaging unit comprising—packed separately from each other — a) at least one container (C1) containing an agent for oxidative hair coloring according to one of the points 1 to 16, and b) at least one container (C2) containing an oxidizing agent preparation (M2), which contains from about 40-96% by weight, preferably from about 70-93% by weight, particularly preferably from about 80-90% by weight, water, furthermore hydrogen peroxide in a total amount of from about 0.5 to about 23% by weight, more preferably from about 2.5 to about 13% by weight, particularly preferably from about 3 to about 10% by weight, of hydrogen peroxide. % by weight, more preferably from about 6 to about 9% by weight, and has a pH value in the range from about 2.0 to about 6.5, preferably from about 2.5-5.5, more preferably from about 2.8 to about 5.0, in each case measured at 20° C., the percentages by weight being based in each case on the weight of the oxidizing agent preparation (M2).

18. Packaging unit (kit-of-parts) according to point 17, wherein the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7% by weight. % by weight, particularly preferably from about 0.5-6% by weight, extremely preferably from about 1-4.5% by weight, in each case based on the weight of the oxidizing agent preparation (M2), and preferably contains no cationic surfactant.

19. Kit-of-parts according to point 18, wherein the oxidizing agent preparation (M2) comprises at least one crosslinked copolymer selected from—Methacrylic acid/methyl acrylate, methacrylic acid/ethyl acrylate, methacrylic acid/propyl acrylate, methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of from about 0.1-7 wt.-%, particularly preferably from about 0.5-6 wt. %, extremely preferably from about 1-4.5 wt. %, each based on the weight of the oxidant preparation (M2), and contains no cationic surfactant.

20. Kit-of-parts according to one of the points 17-19, wherein the oxidizing agent preparation (M2) comprises at least one surfactant selected from anionic surfactants and nonionic surfactants and mixtures thereof in a total amount of from about 0.05-2 wt. %, preferably from about 0.3-1.5 wt. % and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol), 1-eicosanol (arachyl alcohol) and 1-docosanol and mixtures thereof, in a total amount of from about 1-5% by weight. % by weight, preferably from about 1.5-4% by weight, all quantities being based on the weight of the oxidant preparation (M2).

21. Packaging unit (kit-of-parts) according to one of the points 17-20, wherein the oxidant preparation (M2) contains at least one oil in a total amount of from about 0.2-50% by weight, preferably from about 2-40% by weight, particularly preferably from about 8-30% by weight, extremely preferably from about 15-25% by weight, each based on the weight of the oxidant preparation (M2).

22. Packaging unit (kit-of-parts) according to one of the points 17, 20 or 21, wherein the oxidant preparation (M2) contains at least one cationic surfactant, preferably in a total amount of from about 0.05-3 wt. %, particularly preferably of from about 0.1-1.5 wt. %, extremely preferably of from about 0.3-0.9 wt. %, in each case based on the weight of the oxidant preparation (M2).

23. Packaging unit (kit-of-parts) according to one of the points 17 or 21-22, wherein the oxidizing agent preparation (M2) does not contain a polymer with a degree of polymerization of at least about 200 and does not contain a polymer with a molecular weight of 10000 Dalton or higher.

24. Packaging unit (kit-of-parts) according to one of the points 17 to 21 or 23, wherein the oxidizing agent preparation (M2) does not contain cationic surfactants.

25. Kit-of-parts according to one of the points 17 to 24, wherein the finished application mixture of (M1) and (M2) has a pH value in the range from about 6.0-8.0, preferably from about 6.5-7.5, each measured at 20° C.

26. Process for oxidative hair lightening or hair coloring, comprising the following process steps:
i) Provision of a cosmetic product for oxidative hair coloring (M1) according to one of the points 1 to 16,
ii) Provision of an oxidizing agent preparation (M2), containing 40-96 wt. %, preferably from about 70-93 wt. %, more preferably from about 80-90 wt. %, water, further hydrogen peroxide in a total amount of from about 0.5 to about 23 wt. %, more preferably from about 2.5 to about 13 wt. %, particularly preferably from about 3 to about 10% by weight, very particularly preferably from about 6 to about 12% by weight and extremely preferably from about 6 to about 9% by weight, and having a pH value in the range from about 2.0 to about 6.5, preferably from about 2.5-5.5, particularly preferably from about 2.8 to about 5.0, in each case measured at 20° C.,
wherein optionally at least one copolymer selected from cross-linked acrylic acid/acrylic acid -C1-C6-alkyl ester copolymers and cross-linked methacrylic acid/acrylic acid-C1-C6-alkyl ester copolymers may be contained, preferably in a total amount of from about 0.1-7% by weight, particularly preferably from about 0.5-6% by weight, extremely preferably from about 1-4.5% by weight, and preferably no cationic surfactant may be contained, where all quantities refer to the weight of the oxidant preparation (M2),
iii) Mixing of the cosmetic agent (M1) with the oxidizing agent preparation (M2), preferably in a weight ratio (M1):(M2) in the range of from about 0.2:1:to about 3:1, preferably from about 0.3:1 to about 2.5:1, particularly preferably from about 1:1 to about 1.5:1, immediately afterwards
iv) Apply the mixture obtained in step iii) to the hair and leave this mixture on the hair for a period of from about 1 to about 60 minutes, preferably from about 20 to about 45 minutes, at room temperature and/or at from about 30-60° C.,
v) rinsing the hair with water and/or a cleansing composition, and
vi) if necessary, apply an after-treatment agent to the hair and rinse if necessary, followed by drying.

27. Process according to point 26, wherein the finished application mixture of (M1) and (M2) has a pH value in the range of from about 6.0-8.0, preferably from about 6.5-7.5, each measured at 20° C.

28. Process for oxidative hair lightening or hair coloring according to one of the points 26 or 27, wherein the oxidizing agent preparation (M2) is formed as in one of the points 17-25.

The following examples are intended to illustrate the subject matter of the present disclosure, without restricting it thereto.

TABLE 1

Coloring creams for oxidative hair dyeing (all amounts in % by weight)

| Ingredient | E1 |
|---|---|
| Octyldodecanol | 4.00 |
| Sodium laureth(2) sulphate | 2.70 |
| Monoethanolamine | 1.92 |
| p-toluylenediamine sulphate | 1.40 |
| Sodium polyacrylate** | 1.00 |
| Coconut alcohol | 0.75 |
| Paraffinum Liquidum (mineral oil) | 0.74 |
| m-Aminophenol | 0.32 |
| Phenoxyethanol | 1.00 |
| Acrylates/C10-30 alkyl acrylate crosspolymer | 0.40 |
| Ascorbic acid | 0.10 |
| 2-methylresorcinol | 0.16 |
| 4-chlororesorcinol | 0.24 |
| Sodium sulphite | 0.40 |
| 2-amino-3-hydroxypyridine | 0.05 |
| Etidronic acid | 0.12 |
| Trideceth-6 | 0.10 |
| 2-amino-4-[(2-hydroxyethyl)amino]-anisole | 0.10 |
| Perfume | 0.50 |

TABLE 1-continued

Coloring creams for oxidative hair dyeing (all amounts in % by weight)

| Ingredient | E1 |
|---|---|
| C11-13 Isoparaffin | 0.06 |
| 4-hydroxyacetophenone | 0.30 |
| Water | 83.64 |
| Viscosity [mPas]*** | 7000 mPas |
| pH value (20° C.) | 8.3 |

\* Raw material "Synative AL T" from BASF; INCI: Coconut alcohol; C10 and shorter: max. 3% by weight, C12: 48-58% by weight, C14: 18-24 weight %, C16: 8-12 weight %, C18: 11-15% by weight, C20: max. 1% by weight
\*\*Sodium polyacrylate with molar mass Mw ranging from 1.000.000 to 20.000.000 Dalton, pregelatinized in a water-in-mineral oil emulsion with Trideceth-6 as emulsifier
\*\*\*Viscosity: each measured at 20° C. with a Haake VT 550 rotational viscometer, measuring system SV

TABLE 2

Oxidizing agent containing developer for the coloring cream from table 1

| Ingredient | Sample weight (wt.-%) |
|---|---|
| Sodium benzoate | 0.04 |
| Disodium pyrophosphate | 0.30 |
| Na$_2$-EDTA | 0.15 |
| Phosphoric acid (85% by weight) | 0.04 |
| Sodium cetaryl sulphate | 0.20 |
| Cetearyl alcohol | 1.70 |
| PEG-40 Castor Oil | 0.40 |
| Hydrogen peroxide | 9.00 |
| Water | ad 100.00 |

Viscosity: 2500 mPas, measured at 20° C. with a rotational viscometer (Haake VT 550) with measuring system MV II

TABLE 3

Oxidizing agent containing developer for dyeing creams from table 1

| Ingredient | Sample weight (wt.-%) |
|---|---|
| Sodium hydroxide | 0.40 |
| Dipicolinic acid (2,6-dicarboxypyridine) | 0.10 |
| Disodium pyrophosphate | 0.03 |
| Etidronic acid | 0.15 |
| Mixture of cross-linked (meth)acrylic acid/acrylic acid-C1-C6-alkyl ester copolymers (ex Aculyn 33A) | 4.20 (Active) |
| Sodium laureth(2) sulphate | 0.50 |
| Hydrogen peroxide | 6.00 |
| Water | ad 100.00 |

\* Aculyn 33A: aqueous dispersion of acrylate copolymer (mixture of crosslinked (meth)acrylic acid/acrylic acid-C1-C6-alkyl ester copolymers); 28% by weight polymer content (active substance)

Viscosity: 200 mPas, measured at 20° C. with a Brookfield rotational viscometer at a rotation frequency of 20 min$^{-1}$ with spindle 2

TABLE 4

Oxidizing agent containing developer for dyeing creams from table 1

| Ingredient | Sample weight (wt.-%) |
|---|---|
| Sodium benzoate | 0.04 |
| Dipicolinic acid (2,6-dicarboxypyridine) | 0.10 |
| Disodium pyrophosphate | 0.10 |
| Potassium hydroxide | 0.10 |
| 1.2-propanediol | 0.50 |
| Etidronic acid | 0.15 |
| Paraffin oil | 2.00 |
| Cetearyl alcohol | 3.40 |
| Ceteareth-20 | 1.00 |
| Hydrogen peroxide | 6.00 |
| Water | ad 100.00 |

Viscosity: 3,500 mPas, measured at 20° C. with a rotational viscometer (Haake VT 550) at a rotation frequency of 4 min-1 with measuring geometry MV II

TABLE 5

Oxidizing agent containing developer for dyeing creams from table 1

| Ingredient | Sample weight (wt.-%) |
|---|---|
| Sodium benzoate | 0.04 |
| Dipicolinic acid (2,6-dicarboxypyridine) | 0.10 |
| Disodium pyrophosphate | 0.10 |
| Potassium hydroxide | 0.10 |
| 1.2-propanediol | 1.00 |
| Etidronic acid | 0.15 |
| Paraffin oil | 0.30 |
| Stearyl trimethylammonium chloride | 0.30 |
| Cetearyl alcohol | 3.40 |
| Ceteareth-20 | 1.00 |
| Hydrogen peroxide | 6.00 |
| Water | ad 100.00 |

Viscosity: 4,500 mPas, measured at 20° C. with a rotational viscometer (Haake VT 550) at a rotation frequency of 4 min-1 with measuring geometry MV II

TABLE 6

Oxidizing agent containing developer for the coloring cream from table 1

| Ingredient | Sample weight (wt.-%) |
|---|---|
| Sodium benzoate | 0.04 |
| Dipicolinic acid (2,6-dicarboxypyridine) | 0.10 |
| Disodium pyrophosphate | 0.10 |
| Potassium hydroxide | 0.12 |
| Etidronic acid | 0.15 |
| Paraffin oil | 20.00 |
| Sodium cetaryl sulphate | 0.36 |
| Cetearyl alcohol | 3.50 |
| PEG-40 Castor Oil | 0.70 |
| Hydrogen peroxide | 6.00 |
| Water | ad 100.00 |

Viscosity: 7,500 mPas, measured at 20° C. with a rotational viscometer (Haake VT 550) at a rotation frequency of 4 min-1 with measuring geometry MV II

TABLE 7

Oxidizing agent containing developer for the coloring cream from table 1

| Ingredient | Sample weight (wt.-%) |
| --- | --- |
| Sodium benzoate | 0.04 |
| Disodium pyrophosphate | 0.10 |
| Potassium hydroxide | 0.12 |
| Etidronic acid | 0.15 |
| Sodium cetaryl sulphate | 0.20 |
| Cetearyl alcohol | 1.70 |
| PEG-40 Castor Oil | 0.40 |
| Hydrogen peroxide | 6.00 |
| Water | ad 100.00 |

Viscosity: 2500 mPas, measured at 20° C. with a rotational viscometer (Haake VT 550) with measuring system MV II Production of Application Mixtures and Coloring on Hair Dyeing gel and developer according to table 2 were homogeneously mixed in the weight ratio 5:2 (5 parts dyeing gel to 2 parts developer). The application mixture thus obtained was applied to strands of human hair (natural white hair, Kerling company) immediately after production (liquor ratio 4 grams of application mixture per gram of hair) and left on the hair for 30 minutes at room temperature (22° C.). The strands were then rinsed out and dried with a towel.

TABLE 8

Coloring creams for oxidative hair dyeing (all amounts in % by weight)

| Ingredient | E1 |
| --- | --- |
| Octyldodecanol | 4.00 |
| Sodium laureth(2) sulphate | 2.70 |
| Monoethanolamine | 1.62 |
| N,N-bis(2-hydroxyethyl)-p-phenylenediamine sulphate | 0.40 |
| Sodium polyacrylate** | 1.00 |
| Coconut alcohol | 0.75 |
| Paraffinum Liquidum (mineral oil) | 0.74 |
| m-Aminophenol | 0.04 |
| Phenoxyethanol | 1.00 |
| Acrylates/C10-30 alkyl acrylate crosspolymer | 0.40 |
| Ascorbic acid | 0.10 |
| 2-methylresorcinol | 0.10 |
| 2,7-Dihydroxynaphthalene | 0.04 |
| Sodium sulphite | 0.40 |
| Etidronic acid | 0.12 |
| Trideceth-6 | 0.10 |
| Perfume | 0.50 |
| C11-13 Isoparaffin | 0.06 |
| 4-hydroxyacetophenone | 0.30 |
| Sulphuric acid (active substance) | 0.29 |
| Water | 85.34 |
| Viscosity [mPas]*** | 7000 mPas |
| pH value (20° C.) | 8.3 |

* Raw material "Synative AL T" from BASF; INCI: Coconut alcohol; C10 and shorter: max. 3% by weight, C12: 48-58% by weight, C14: 18-24 weight %, C16: 8-12 weight %, C18: 11-15% by weight, C20: max. 1% by weight
**Sodium polyacrylate with molar mass Mw ranging from 1.000.000 to 20.000.000 Dalton, pregelatinized in a water-in-mineral oil emulsion with Trideceth-6 as emulsifier
***Viscosity: each measured at 20° C. with a Haake VT 550 rotational viscometer, measuring system SV

TABLE 9

Production of application mixtures for coloring hair

| alkaline staining cream (M1) | Developer (M2) | Weight ratio (M1):(M2) | Viscosity of the application mixture [mPas]** | pH value (20° C.) |
| --- | --- | --- | --- | --- |
| according to Table 1 | according to Table 2 | 1:1 | 11,000 | 7.5 |
| according to Table 8 | according to Table 2 | 1:1 | 11,000 | 7.9 |

**Viscosity: measured at 20° C. (Haake rotational viscometer VT 550, measuring system MV II).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for oxidative hair lightening or hair coloring comprising, in each case based on the weight of the agent,
    from about 70-90% by weight water,
    at least one alkalizing agent,
    at least one crosslinked copolymer of acrylic acid and non-ethoxylated esters of acrylic acid with linear C10-C30 monoalcohols as monomers, the crosslinked copolymer being present in a total amount of from about 0.3-0.5% by weight,
    at least one linear, saturated 1-alkanol with one hydroxy group and from about 8 to about 22 carbon atoms in a total amount of from about 0.3-1.5% by weight,
    at least one anionic surfactant in a total amount of from about 1-6% by weight, and
    optionally at least one coloring substance selected from oxidation dye precursors, direct-acting hair dyes and mixtures thereof,
    sodium polyacrylate,
    wherein the agent is free from oxidizing agents, and
    wherein the agent has a pH value in the range from about 7.5 to about 9.5, measured at 20° C.

2. The agent according to claim 1, wherein the alkalizing agent is selected from the group of ammonium hydroxide, basic amino acids, alkali hydroxides, alkanolamines, alkali metal metasilicates, alkali phosphates, alkali hydrogen phosphates, and mixtures thereof.

3. The agent according to claim 1, wherein the at least one anionic surfactant is selected from the group of $C_8$-$C_{20}$ alkyl sulphates, $C_8$-$C_{20}$ alkyl ether sulphates and $C_8$-$C_{20}$ ether carboxylic acids, each with about 8 to about 20 C atoms in the alkyl group and from 0 to about 12 ethylene oxide groups in the molecule.

4. The agent according to claim 1, wherein the at least one crosslinked copolymer of acrylic acid and non-ethoxylated esters of acrylic acid with linear C10-C30 monoalcohols is selected from copolymers with the INCI designation acrylates/C10-30 alkyl acrylates crosspolymer.

5. The agent according to claim 1, having a viscosity in the range of from about 3,000-25,000 mPas, as measured at 20° C. with a Haake VT 550 rotational viscometer, measuring system SV.

6. The agent according to claim 1, further comprising at least one nonionic surfactant.

7. The agent according to claim 1, further comprising at least one cationic or zwitterionic polymer selected from polyquaternium-22, polyquaternium-39, acrylamidopropyltrimonium chloride/acrylate copolymer, polyquaternium-6, or mixtures thereof.

8. The agent according to claim 1, further comprising at least one oil.

9. The agent according to claim 1, wherein the at least one linear, saturated 1-alkanol with one hydroxy group and 8 to 22 carbon atoms is selected from the group of lauryl alcohol, coconut alcohol, 1-tetradecanol, cetyl alcohol, stearyl alcohol or mixtures thereof.

10. The agent according to claim 1, further comprising at least one nonionic surfactant in a total amount of from about 0.01-1% by weight based on the weight of the agent.

11. The agent according to claim 1, further comprising at least one oil selected from natural and synthetic hydrocarbons; triglycerides of linear or branched, saturated or unsaturated, optionally hydroxylated $C_{8-30}$ fatty acids; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids with monovalent linear, branched or cyclic $C_2$-$C_{18}$ alkanols or with polyvalent linear or branched $C_2$-$C_6$ alkanols; silicone oils; or mixtures of the above substances.

12. The agent according to claim 1, further comprising at least one coloring substance selected from oxidation dye precursors.

13. Kit-of-parts packaging unit comprising—packed separately from each other—
a) at least one container (C1) comprising an agent for oxidative hair lightening or hair coloring according to claim 1, and
b) at least one container (C2) comprising an oxidizing agent preparation (M2), which comprises from about 40-96% by weight water, hydrogen peroxide in a total amount of 0.5 to 23% by weight, and has a pH value in the range from 2.0 to 6.5 measured at 20° C., the percentages by weight being based in each case on the weight of the oxidizing agent preparation (M2).

14. Process for oxidative hair lightening or hair coloring, comprising the following process steps:
i) preparing a cosmetic composition for oxidative hair coloring (M1) according to claim 1,
ii) providing an oxidizing agent preparation (M2) comprising from about 40-96 wt. % water, hydrogen peroxide in a total amount of from about 0.5 to about 23 wt. %, and having a pH value in the range from about 2.0 to about 6.5 measured at 20° C.,
iii) wherein (M2) optionally comprises at least one copolymer selected from cross-linked acrylic acid/acrylic acid-C1-C6-alkyl ester copolymers or cross-linked methacrylic acid/acrylic acid-C1-C6-alkyl ester copolymers, wherein amounts are based on the weight of the oxidant preparation (M2),
iv) mixing the cosmetic agent (M1) with the oxidizing agent preparation (M2),
v) applying the mixture obtained in step iii) to the hair and leave this mixture on the hair for a period of from about 1 to about 60 minutes,
vi) rinsing the hair with water and/or a cleansing composition, and
vii) optionally, applying an after-treatment agent to the hair and optionally rinsing, followed by drying.

15. The agent according to claim 1, comprising:
from about 76-84% by weight water,
the crosslinked copolymer present in a total amount of from about 0.4-0.45% by weight,
the at least one linear, saturated 1-alkanol with one hydroxy group and from about 8 to about 22 carbon atoms present in a total amount of from about 0.6-0.8% by weight, and
the at least one anionic surfactant present in a total amount of from about 2.5-4.5% by weight.

16. The agent according to claim 1, wherein the sodium polyacrylate has a mass-average molar mass Mw in the range of 1,000,000 to 20,000,000 Daltons and is present in a total amount of from about 0.1-1.5wt.-%, based on the weight of the agent.

17. The agent according to claim 16, wherein the sodium polyacrylate is included pregelled in a water-in-oil emulsion.

18. The agent according to claim 1, comprising the crosslinked copolymer present in a total amount of from about 0.4-0.45% by weight based on the weight of the agent.

19. The agent according to claim 1, further comprising 4-hydroxyacetophenone.

20. The kit-of-parts according to claim 13, wherein the agent for oxidative hair lightening or hair coloring in the at least one container a) has a viscosity in the range of from about 6,000-12,000 mPas and the oxidizing agent preparation (M2) has a viscosity in the range of about 10 to about 6,000 mPas, both as measured at 20° C. with a Haake VT 550 rotational viscometer, measuring system SV.

* * * * *